(12) United States Patent
Lagunavicius et al.

(10) Patent No.: US 10,435,675 B2
(45) Date of Patent: Oct. 8, 2019

(54) POLYMERASE COMPOSITIONS AND USES

(71) Applicant: Thermo Fisher Scientific Baltics UAB, Vilnius (LT)

(72) Inventors: Arunas Lagunavicius, Vilnius (LT); Arvydas Janulaitis, Vilnius (LT)

(73) Assignee: Thermo Fisher Scientific Baltics UAB (LT)

( * ) Notice: Subject to any disclaimer, the term of this patent is extended or adjusted under 35 U.S.C. 154(b) by 0 days.

(21) Appl. No.: 15/421,870

(22) Filed: Feb. 1, 2017

(65) Prior Publication Data

US 2017/0267982 A1   Sep. 21, 2017

Related U.S. Application Data

(62) Division of application No. 12/878,159, filed on Sep. 9, 2010, now Pat. No. 9,598,679.

(30) Foreign Application Priority Data

Sep. 9, 2009 (GB) .................................. 0915796.7

(51) Int. Cl.
*C12N 9/12* (2006.01)
*C12N 9/96* (2006.01)

(52) U.S. Cl.
CPC .............. *C12N 9/1252* (2013.01); *C12N 9/96* (2013.01)

(58) Field of Classification Search
None
See application file for complete search history.

(56) References Cited

U.S. PATENT DOCUMENTS

| | | | |
|---|---|---|---|
| 5,248,940 A | 9/1993 | Patience et al. | |
| 5,489,523 A | 2/1996 | Mathur | |
| 6,127,155 A | 10/2000 | Gelfand et al. | |
| 6,242,235 B1 | 6/2001 | Shultz et al. | |
| 6,433,017 B1 | 8/2002 | Felgner et al. | |
| 7,030,220 B1 | 4/2006 | Ankenbauer et al. | |
| 7,422,882 B2 | 9/2008 | Kuroita et al. | |
| 7,452,665 B2 | 11/2008 | Barnes | |
| 7,855,055 B2 * | 12/2010 | Barnes ................... | C12Q 1/686 435/5 |
| 2003/0134292 A1 | 7/2003 | Farchaus, III | |
| 2008/0145910 A1 | 6/2008 | Ward | |

FOREIGN PATENT DOCUMENTS

| | | |
|---|---|---|
| EP | 1970440 | 9/2008 |
| WO | WO 2000/068411 | 11/2000 |
| WO | WO 2007/123689 | 11/2007 |
| WO | WO 2008/013885 | 1/2008 |
| WO | WO 2008/077017 | 6/2008 |

OTHER PUBLICATIONS

Barik, S., "Site-Directed Mutagenesis by Double Polymerase Chain Reaction," Molecular Biotechnology, 1995, 3, pp. 1-7.
Eom, S. et al., "Structure of Taq Polymerase with DNA at the Polymerase Active Site," Nature, 1996, 382, pp. 278-281.
Great Britain Search Report for GB0915796.7, dated Jan. 4, 2010, 1 page.
International Search Report and Written Opinion for PCT/EP2010/063223, dated Mar. 7, 2011, 7 pages.
Ishino, Y., et al., "The Amino Acid Sequence Required for 5' → 3' Exonuclease Activity of *Bacillus Caldotenax* DNA Polymerase", Protein Engineering, 1995, 8:1, pp. 1171-1175.
Lagunavicius, A. et al., "The Metal-independent Type IIs Restriction Enzyme B fi I is a Dimer that Binds Two DNA Sites but has Only One Catalytic Centre," J. Mol. Biol., 2003, 326, pp. 1051-1064.
Noinville, S., et al., "Conformational Changes of Enzymes Absorbed at Liquid-Solid Interface: Relevance to Enzymatic Activity," Biopolymers (Biospectroscopy), 2002, vol. 67, pp. 323-326.
Phusion® DNA Polymerase Products. Finnzymes Tools for Molecular Biology Website http://www.finnzymes.com/pcr/phusion_products.html Jan. 13, 2011.
Phusion® DNA Polymerase Products. Finnzymes Reagents—Products—Phusion® Website http://www.replay.waybackmachine.org/20080723103957/http:/finnzymes.com/pcr/p . . . Jun. 4, 2011.
Prakash, A.R., et al., "Characteristics and Impact of Taq Enzyme Adsorption on Surfaces in Microfluidic Devices," Microfluid Nanofluid, 2008, 4, pp. 295-305.
Riggs, M.G. et al., "Construction of Single Amino Acid Substitution Mutants of Cloned *Bacillus Stearothermophilus* DNA Polymerase I which lack 5' → 3' Exonuclease Activity," Biochemica et Biophysica Acta, 1996, 1307, pp. 178-186.
Sasaki, Y. et al., "Effect of Molecular Crowding on DNA Polymerase Activity," Biotechnology Journal, 2006, 1:4, pp. 440-446.
Steuerwald, N. et al., Analysis of Gene Expression in Single Oocytes and Embryos by Real-Time Rapid Cycle Fluorescence Monitored RT-PCR, Molecular Human Reproduction, 1999, 5:11, pp. 1034-1039.
Vu et al., "Gold Nanoparticle Effects in Polymerase Chain Reaction: Favoring of Smaller Products by Polymerase Adsorption," Analytical Chemistry, 2008, vol. 80, pp. 5462-5467.
Wang et al., "Silicon Inhibition Effects on the Polymerase Chain Reaction: A Real-Time Detection Approach," Journal of Biomedical Materials Research A, 2006, vol. 77, pp. 28-34.
File History of U.S. Appl. No. 12/878,159, filed Sep. 9, 2010.

* cited by examiner (Continued)

Primary Examiner — Richard G Hutson

(57) ABSTRACT

A composition having nucleic acid polymerase activity, which comprises an active nucleic acid polymerase and an excess amount of a non-functional mutant nucleic acid polymerase protein, wherein the non-functional mutant nucleic acid polymerase protein stabilizes the active nucleic acid polymerase against loss of polymerase activity.

20 Claims, 40 Drawing Sheets

Specification includes a Sequence Listing.

(Example 1)

(Example 2)

(Example 2)

(Example 2)

(Example 3)

(Example 4)

(Example 5)

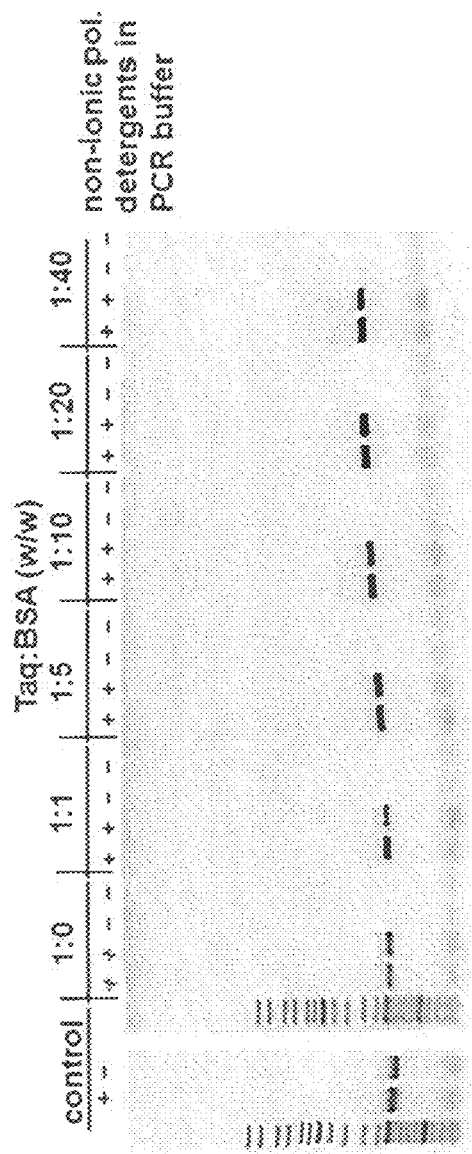
Fig. 6 (Example 5)

(Example 6)

(Example 6)

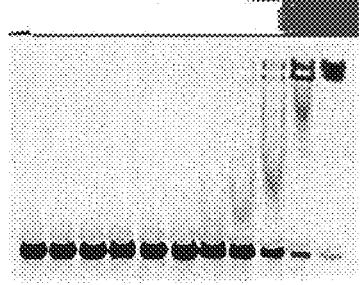 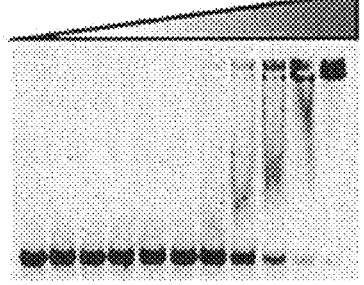
(Example 6)
Fig. 7E  Fig. 7F (Example 6)

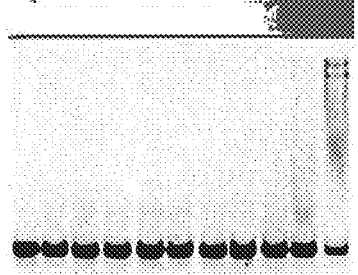
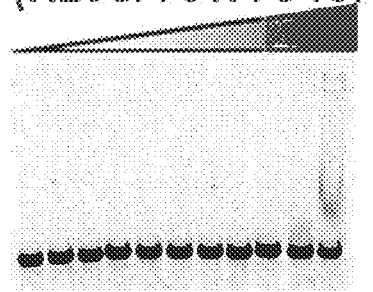
(Example 6)
Fig. 7I                    Fig. 7J (Example 6)

(Example 6)

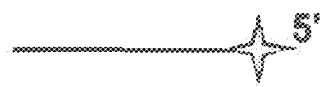
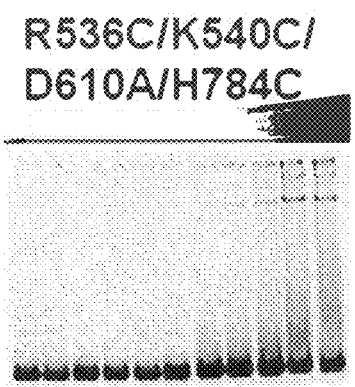 
(Example 6)
Fig. 8E  Fig. 8F (Example 6)

 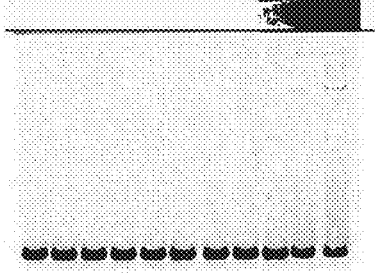
(Example 6)
Fig. 8I  Fig. 8J (Example 6)

(Example 7)

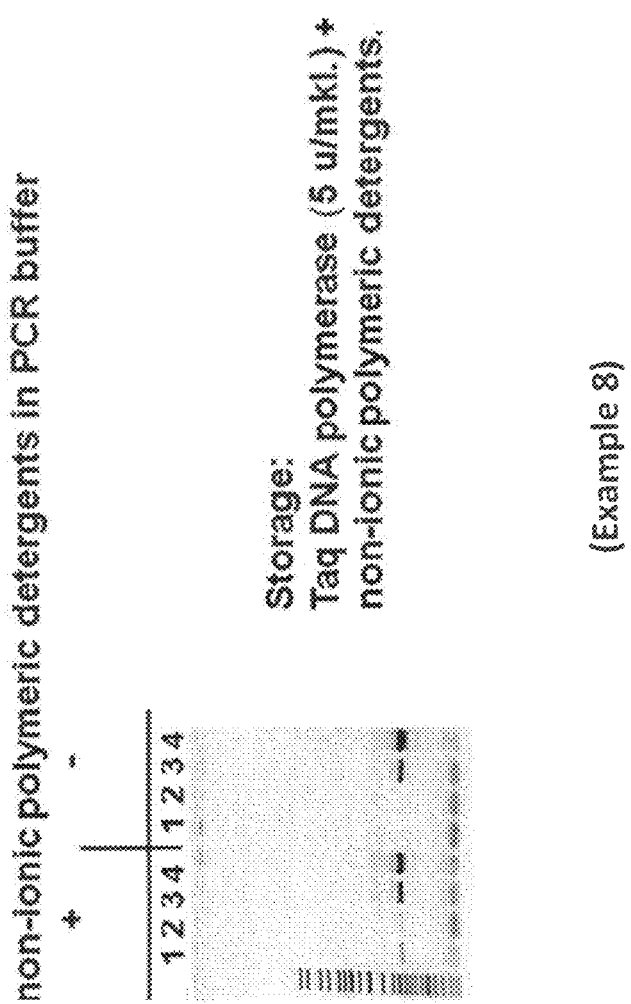

(Example 8)

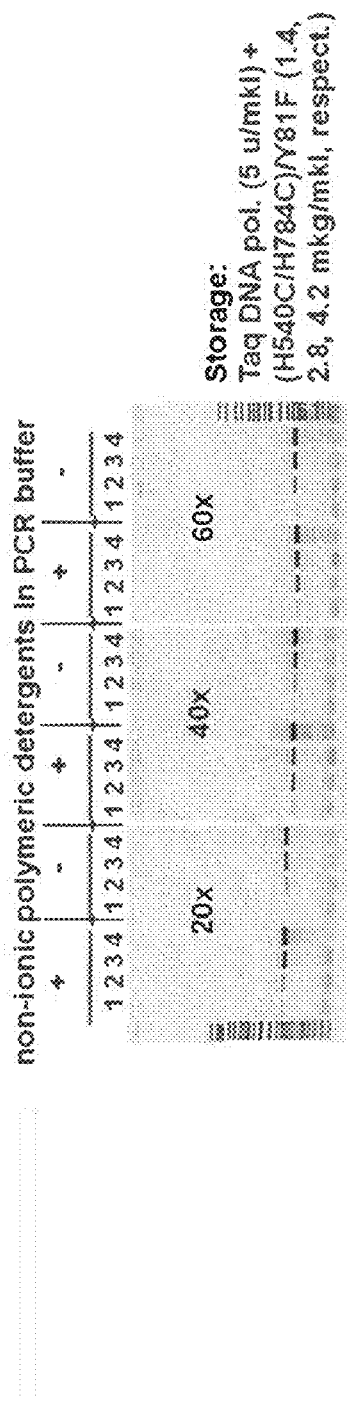
Fig. 11C (Example 8)

(Example 8)

(Example 9)

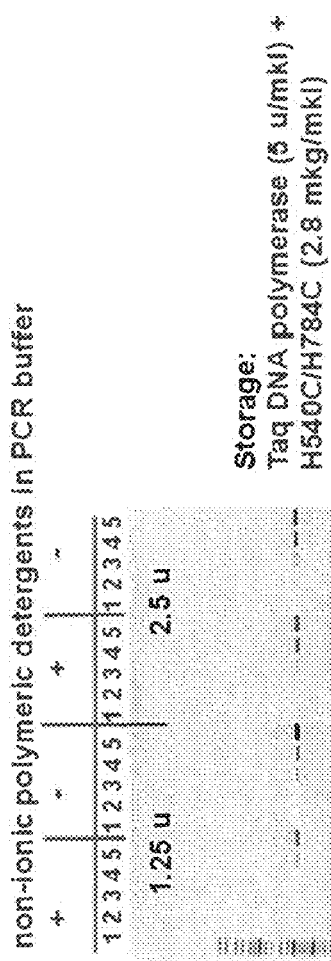

non-ionic polymeric detergents in PCR buffer

- + - + - +
1 2 3 4 5 | 1 2 3 4 5 | 1 2 3 4 5 | 1 2 3 4 5 | 1 2 3 4 5 | 1 2 3 4 5
1.25 u | 2.5 u

Storage:
Taq DNA polymerase (5 u/mkl) +
(H540C/H784C)/Y81F (2.8 mkg/mkl)

(Example 9)

Fig. 12C non-ionic polymeric detergents in PCR buffer

Storage:
Taq DNA polymerase (5 u/mkl) +
(H540C/H784C)/R25S (2.8 mkg/mkl)

(Example 9)

Fig. 12D (Example 10)

(Example 11)

Fig. 15 (Example 12)

(Example 13)

(Example 14)

(Example 15)

(Example 16)

(Example 17)

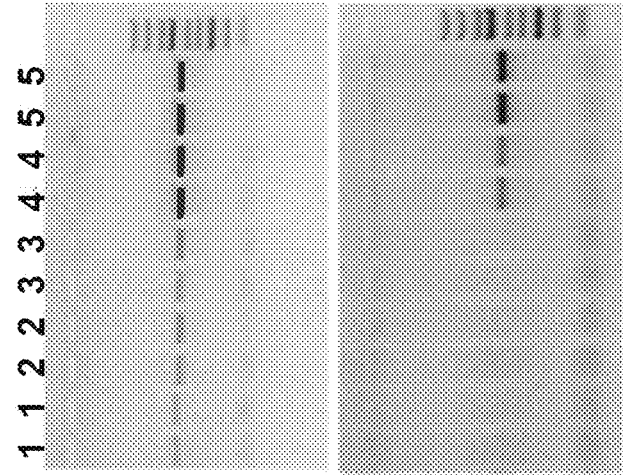
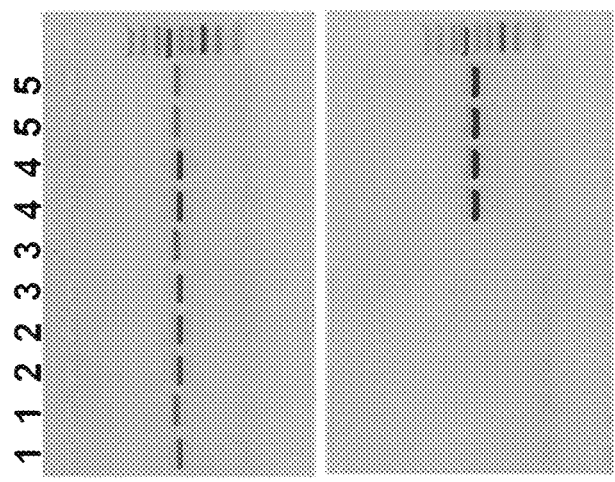
Fig. 21A Fig. 21B Fig. 21C Fig. 21D
(Example 18)

SEQUENCE LISTING

<160> NUMBER OF SEQ ID NOS: 14

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
gctgcatcat ataagttgcc					20

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
aaggctacac tgttaatttt					20

<210> SEQ ID NO 3
<211> LENGTH: 24
<212> TYPE: DNA
<213> ORGANISM: Artificial Sequence
<220> FEATURE:
<223> OTHER INFORMATION: Oligonucleotide

<400> SEQUENCE: 3
ttttagccgc tagagtcgac ctgc					24

<210> SEQ ID NO 4
<211> LENGTH: 44
<212> TYPE: DNA
<213> ORGANISM: Artificial Sequence
<220> FEATURE:
<223> OTHER INFORMATION: Oligonucleotide

<400> SEQUENCE: 4
ggagacaagc ttgtatgcct gcaggtcgac tctagcggct aaaa					44

<210> SEQ ID NO 5
<211> LENGTH: 24
<212> TYPE: DNA
<213> ORGANISM: Artificial Sequence
<220> FEATURE:
<223> OTHER INFORMATION: Oligonucleotide

<400> SEQUENCE: 5
ttttagccgc tagagtcgac ctgc					24

<210> SEQ ID NO 6
<211> LENGTH: 22
<212> TYPE: DNA
<213> ORGANISM: Artificial Sequence
<220> FEATURE:
<223> OTHER INFORMATION: M13/pUC Sequencing Primer

<400> SEQUENCE: 6
gccagggttt tcccagtcac ga					22

<210> SEQ ID NO 7
<211> LENGTH: 24
<212> TYPE: DNA
<213> ORGANISM: Artificial Sequence

```
<220> FEATURE:
<223> OTHER INFORMATION: M13/pUC Reverse Sequencing Primer

<400> SEQUENCE: 7
gagcggataa caatttcaca cagg                                              24

<210> SEQ ID NO 8
<211> LENGTH: 17
<212> TYPE: DNA
<213> ORGANISM: Artificial Sequence
<220> FEATURE:
<223> OTHER INFORMATION: pASK Reverse Primer

<400> SEQUENCE: 8
cgcagtagcg gtaaacg                                                      17

<210> SEQ ID NO 9
<211> LENGTH: 19
<212> TYPE: DNA
<213> ORGANISM: Artificial Sequence
<220> FEATURE:
<223> OTHER INFORMATION: agseq5 Primer

<400> SEQUENCE: 9
attccctcca tactcgggg                                                    19

<210> SEQ ID NO 10
<211> LENGTH: 21
<212> TYPE: DNA
<213> ORGANISM: Artificial Sequence
<220> FEATURE:
<223> OTHER INFORMATION: PGK1 Direct Primer

<400> SEQUENCE: 10
agctgctggg tctgtcatcc t                                                 21

<210> SEQ ID NO 11
<211> LENGTH: 23
<212> TYPE: DNA
<213> ORGANISM: Artificial Sequence
<220> FEATURE:
<223> OTHER INFORMATION: PGK1 Reverse Primer

<400> SEQUENCE: 11
atcttttccc ttcccttctt cct                                               23

<210> SEQ ID NO 12
<211> LENGTH: 22
<212> TYPE: DNA
<213> ORGANISM: Artificial Sequence
<220> FEATURE:
<223> OTHER INFORMATION: PGK Probe

<400> SEQUENCE: 12
tggagaacct ccgctttcat gt                                                22

<210> SEQ ID NO 13
<211> LENGTH: 19
<212> TYPE: DNA
<213> ORGANISM: Artificial Sequence
<220> FEATURE:
<223> OTHER INFORMATION: HPRT-3' Primer

<400> SEQUENCE: 13
gctggtgaaa aggacctct                                                    19
```

```
<210> SEQ ID NO 14
<211> LENGTH: 20
<212> TYPE: DNA
<213> ORGANISM: Artificial Sequence
<220> FEATURE:
<223> OTHER INFORMATION: HPRT-5' Primer

<400> SEQUENCE: 14
cacaggacta gaacacctgc                                              20
```

POLYMERASE COMPOSITIONS AND USES

This application is a divisional of U.S. application Ser. No. 12/878,159, filed Sep. 9, 2010, which claims priority from GB Application No. 0915796.7 filed Sep. 9, 2009, each of which is incorporated by reference herein in its entirety for any purpose.

The material contained in the accompanying computer readable Sequence Listing identified as Sequence_Listing.txt, having a file creation date of Jan. 30, 2017, and file size of 2.81 KB, is incorporated herein by reference.

FIELD OF THE INVENTION

The present invention relates to a composition having nucleic acid polymerase activity, methods of stabilizing nucleic acid polymerases, methods for amplifying target nucleic acid sequences and kits therefor.

BACKGROUND OF INVENTION

Stable commercial preparations of thermophilic polymerases that retain during storage and in reaction mixtures the same level of the enzymatic activity are necessary for their use in many biochemical processes or diagnostics. Thermophilic polymerases can be native (isolated from naturally found thermophilic microorganisms) or recombinant (isolated from the bacterial host harbouring cloned gene encoding said thermophilic polymerase). Due to their origin these enzymes are stable to denaturation by heat. However, even highly thermostable polymerases may be inactivated by chemical agents, proteases, or unfavourable environmental conditions during storage.

Noteworthy, many uses of thermostable enzymes often comprise reaction steps in denaturing conditions, such as highly elevated temperatures, aqueous environments with sub-optimal concentrations of cofactors and substrates, and a pH that is suboptimal for maximum enzyme stability. For example, amplification of nucleic acids involves thermal cycling of a reaction mixture containing a nucleic acid polymerase to generate an amplified target nucleic acid product. An example of a thermal cycling process is Polymerase Chain Reaction (PCR), in which the reaction mixture is subjected to oligonucleotide denaturing, primer annealing, and primer extension reaction temperatures. Thermostable DNA polymerases are generally used to amplify target DNA sequences in said thermal cycling reactions.

Numerous stabilization techniques are known. These techniques include chemical modification of the enzyme, genetic engineering of the enzyme and the addition of stabilizing additives, such as detergents. Detergents are surface active compounds that are conventionally considered to stabilize the interface between the hydrophobic enzyme surface and the hydrophilic liquid environment in which they are contained. For example, U.S. Pat. No. 6,127,155 B1 (included herein as reference) discloses that non-ionic polymeric detergents, such as polyethoxylated sorbitan monolaurate (Tween 20) and ethoxylated alkyl phenol (NP-40) contained in the storage buffer stabilize Taq DNA polymerase. Also, U.S. Pat. No. 6,242,235 B1 discloses polymerase stabilization by polyethoxylated amine surfactants. Also disclosed therein are cationic surfactants for the stabilization of polymerases. Similar compounds have been proposed as polymerase stabilising agents in US patent application US2003/0134292A1.

U.S. Pat. No. 6,242,235 B1 discloses polymerase stabilization by polyethoxylated amine surfactants, while WIPO PCT patent application WO/2008/013885A2 discloses the use of zwitterionic detergents and non-detergent surfactants for the storage and uses of DNA polymerases. EPO patent application EP1970440 A1 discloses stabilization of polymerases in aqueous solutions by ionic, particularly zwitterionic detergents in the presence of inert proteins, such as BSA. WIPO patent application WO/2008/077017A2 discloses compositions, methods, and kits comprising thermostable DNA polymerase and an anionic detergent or a zwitterionic detergent.

All above cited stabilization methods have certain drawbacks, including (i) high denaturing effect, (ii) a positive or negative charge, (iii) a low efficiency in disrupting polymerase protein aggregation and (iv) an often difficult removal of the detergent after the performance of the reaction, especially in cases when presence of detergent is undesirable in downstream applications (e.g. use in microarrays). For example, PCR products used for DHPLC (denaturing high pressure liquid chromatography) analysis are recommended to be free of detergents. Detergents may also cause foaming when PCR products are spotted on microarray slides (www.finnzymes.com/pcr/phusion_products.html).

Thus, there is a need for methods and compositions comprising stabilized thermophilic nucleic acids polymerases, which have low denaturing effect, high efficiency in disrupting aggregation and which need no detergent in case of interference in the further processing of polymerization reaction products.

SUMMARY OF INVENTION

In a first aspect the present invention provides a composition having nucleic acid polymerase activity, which comprises an active nucleic acid polymerase and an excess amount of a non-functional mutant nucleic acid polymerase protein, wherein the non-functional mutant nucleic acid polymerase protein stabilizes the active nucleic acid polymerase against loss of polymerase activity.

In a further aspect, the present invention provides use of a non-functional mutant nucleic acid polymerase protein for stabilizing an active nucleic acid polymerase against loss of polymerase activity.

In a further aspect, the present invention provides a method of stabilizing an active nucleic acid polymerase against loss of polymerase activity, which comprises contacting the active nucleic acid polymerase with an excess amount of a non-functional mutant nucleic acid polymerase protein so as to stabilize the nucleic acid polymerase.

The present applicants have found that the use of surfactants such as non-ionic polymeric detergents in increasing the storage stability and activity of polymerases such as the Taq DNA polymerase most likely acts via decreased enzyme adhesion on hydrophobic surfaces such as those of plastic vials used for enzyme storage and reactions. This contrasts with the conventional view that these surfactants simply stabilize the interface between the hydrophobic enzyme surface and the hydrophilic liquid environment in which they are contained or by stabilizing the interface among several enzyme molecules, which due to their hydrophobic surface tend to aggregate in hydrophilic environment. Surprisingly, the present applicants have found that non-functional mutant nucleic acid polymerase proteins may be used to stabilize active nucleic acid polymerases, especially when they are mutants of the same or a closely related polymerase. This has a number of advantages over conventional methods of stabilization such as those which use detergents or bovine serum albumin (BSA). According to the invention, the use of the non-functional mutant nucleic acid polymerase protein obviates the need for any additional detergent. This is the case both during storage of the active nucleic acid polymerase and when the active nucleic acid polymerase is used in a reaction mixture in, for example, an amplification reaction. As a result, downstream processes which are sensitive to detergent such as DHPLC or use in micro arrays are not adversely affected by the components of upstream reaction mixture.

Nucleic acid polymerase activity according to the invention refers to the ability of a polymerase to synthesize nucleic acid strands from nucleoside triphosphates, for example from a template strand typically in the presence of a primer oligonucleotide capable of hybridising to the template strand. The nucleic acid may refer to RNA or DNA as well as nucleic acids incorporating at least some synthetic analogues of RNA or DNA. The invention is particularly applicable to DNA polymerases wherein the nucleic acid is DNA. Such DNA polymerases include bacterial and archaeal DNA polymerases. The polymerases may be from family A or family B.

The non-functional mutant nucleic acid polymerase protein may be the same as or different from the active nucleic acid polymerase provided that the polymerase activity is absent at least to the extent that the non-functional protein is inactive in a PCR reaction. Accordingly, functionality in PCR is a measurement of activity of the inactivated non-functional polymerase protein; that is, the polymerase activity of inactivated non-functional polymerase protein is such that it does not produce a PCR product. Other activity such as 5' to 3' exonuclease activity may or may not still be present in the non-functional protein. Thus, the polymerase-inactive protein may or may not be catalytically active in some other sense. It is further preferred that the non-functional protein does not bind substrate for the polymerase activity. Otherwise, the inactivated non-functional polymerase protein may have a reduced template-primer substrate or primer binding activity. It is preferred that the non-functional mutant nucleic acid polymerase protein is a mutant version of the active nucleic acid polymerase such as obtainable by site-directed mutagenesis by other mutagenesis methods or by chemical modification. It is also possible to use a closely related protein, such as one having a similar thermal stability. The non-functional mutant nucleic acid polymerase protein preferably retains the physical properties characteristic of the active wild-type polymerase. Such characteristics include thermostability, surface hydrophobicity and other properties.

The excess amount of non-functional mutant nucleic acid polymerase protein needed to stabilize the active nucleic acid polymerase may be determined empirically. An excess amount may be an amount greater than the amount of active nucleic acid polymerase present in the composition and could range from 1:5 to 1:300 and is preferably from 1:10 to 1:60.

According to the invention, the non-functional mutant nucleic acid polymerase protein stabilizes the active nucleic acid polymerase against loss of polymerase activity. Loss of polymerase activity may arise through inactivation of the active polymerase in the sense that the specific activity is reduced or through loss of active protein. Enzyme inactivation may arise through the action of chemical agents, proteases or other environmental conditions, particularly during storage. Enzyme inactivation may arise through the presence of inhibitors of enzyme activity. Such inhibitors may be present in biological samples which contain the substrate for the active enzyme, for example. As described herein, protein loss has been found to arise in particular by adhesion to hydrophobic surfaces such as container walls, especially the walls of vials and other containers made of plastics material. Due to adhesion, polymerase molecules are removed from the solution, therefore leaving a decreased overall polymerase activity in the preparation (composition). This especially has an effect on polymerase activity in storage or reaction compositions with low (working) polymerase concentration. Stabilisation accordingly refers to the ability of the non-functional mutant nucleic acid polymerase protein to inhibit over time a reduction in the activity of the active nucleic acid polymerase. The stabilisation by non-functional polymerase protein present in excess in the vial occurs in part due to the adhesion of the non-functional polymerase protein itself to the walls of vial and thus competing with the active polymerase, which then remains in the solution and is not adhered to the walls of the vial. Stabilisation also includes the ability of a material to maintain or enhance enzyme activity under suboptimal conditions, such as suboptimal pH or temperature, as compared to activity in the absence of the stabilizing compound or material. Suboptimal conditions also include conditions where an inhibitor of the active polymerase is present. Stabilisation may typically be measured by comparing the loss of activity over time in the presence and absence of the non-functional protein selected for stabilisation.

The present invention provides both storage compositions and reaction mixtures. In one arrangement a storage composition is provided which includes the active nucleic acid polymerase and an excess amount of the non-functional mutant nucleic acid polymerase protein. This composition may additionally include a storage buffer and the storage composition may typically be stored at a temperature from ambient to −20 C and less, typical of storage temperatures of other commercial polymerase compositions. The active nucleic acid polymerase may or may not have polymerase activity under all conditions, including storage conditions. However, it is active in the sense that when exposed to appropriate reaction conditions it displays polymerase activity. In a further arrangement a reaction mixture is provided which includes the active nucleic acid polymerase and an excess amount of the non-functional mutant nucleic acid polymerase protein. Such a mixture typically may include a buffer suitable for use in the reaction in which the polymerase is to be used. Other components may also be incorporated in the reaction mixture, such as nucleoside 5' triphosphates in the case of a reaction mixture for an amplification reaction as described in further detail below.

Compositions according to the invention may or may not incorporate a detergent although it is preferred in many cases that the compositions are free of detergents.

The compositions may include a combination of one or more active polymerases together with one or more non-functional mutant polymerases.

Useful nucleic acid polymerases include *Thermus thermophilus* (Tth) DNA polymerase, *Thermotoga neopolitana* (Tne) DNA polymerase, *Thermotoga maritima* (Tma) DNA polymerase, *Thermococcus litoralis* (Tli or VENT™) DNA polymerase, *Pyrococcus furiosus* (Pfu) DNA polymerase, DEEPVENT. DNA polymerase, *Pyrococcus woosii* (Pwo) DNA polymerase, *Pyrococcus* sp KDD2 (KOD) DNA polymerase, *Bacillus sterothermophilus* (Bst) DNA polymerase, *Bacillus caldophilus* (Bca) DNA polymerase, *Sulfolobus acidocaldarius* (Sac) DNA polymerase, *Thermoplasma acidophilum* (Tac) DNA polymerase, *Thermus flavus* (Tfl/Tub) DNA polymerase, *Thermus ruber* (Tru) DNA polymerase,

*Thermus brockianus* (DYNAZYME) DNA polymerase, *Methanobacterium thermoautotrophicum* (Mth) DNA polymerase, and *mycobacterium* DNA polymerase (Mtb, Mlep).

According to one aspect of the invention the active nucleic acid polymerase is a thermophilic nucleic acid polymerase such as Taq DNA polymerase or *thermococcus* sp. DNA polymerase. Thermophilic nucleic acid polymerases typically have a temperature optimum of 70-75° C. and may operate in a range of approximately 50° C. to 90° C. These enzymes are thermostable proteins. Thermostable proteins are typically stable up to a temperature of 95° C.

Compositions according to the invention are particularly useful in amplification reactions such as those which include thermal cycling steps and use thermostable nucleic acid polymerases. In such cases both the active nucleic acid polymerase and the non-functional mutant nucleic acid polymerase protein are thermostable. This means that the stabilizing effect of the non-functional mutant nucleic acid polymerase protein is not reduced owing to high temperature induced denaturation because the non-functional mutant nucleic acid polymerase protein is thermostable. This is an advantage over conventional stabilizers such as conventional proteins which would tend to denature at high temperatures.

Accordingly, in a further aspect, the present invention provides a method for the synthesis or amplification of a target nucleic acid sequence, which comprises
  (a) forming a reaction mixture comprising:
    (i) the target nucleic acid sequence;
    (ii) a composition having nucleic acid polymerase activity as described herein; and
    (iii) nucleoside-5'-triphosphates to support the nucleic acid polymerase activity; and
  (b) subjecting the reaction mixture to conditions to synthesise or amplify the target nucleic acid sequence.

There is further provided the use of a composition as described herein in a method of synthesising or amplifying a target nucleic acid sequence.

There is further provided a kit for the synthesis or amplification of a target nucleic acid sequence, which comprises:
  (a) an active nucleic acid polymerase;
  (b) a non-functional mutant nucleic acid polymerase protein for stabilizing the active nucleic acid polymerase; and
  (c) optionally one or more reagents or buffers for use in a nucleic acid synthesis or amplification method.

The amplification of the target nucleic acid sequence may be achieved by any conventional method. Various synthesis methods may be performed by polymerases that are not necessarily amplification methods, including filling of 3'-recessed ends of DNA, 5'-exonuclease and 3'-exonuclease degradation methods. These methods can be also performed by thermophilic polymerases, such as Taq or *Thermococcus* sp. DNA polymerases. Amplification methods involving a temperature cycling offer a particular use for compositions of the present invention. Such methods include polymerase chain reaction (PCR) and quantitative PCR. In a typical PCR reaction a sample nucleic acid which comprises the target nucleic acid sequence is contacted with the composition having nucleic acid polymerase activity in the presence of the nucleoside-5'-triphosphates as well as one or more primer sequences. A DNA template may be denatured at a temperature in the range 94 to 98° C. so as to yield single-stranded DNA, the reaction temperature is lowered to perhaps 50 to 65° C. to allow annealing of the primers to the single-stranded DNA template. The active nucleic acid polymerase binds to the primer-template hybrid and begins DNA synthesis. Typically the temperature is increased to between 75 to 80° C. to enable the polymerase to perform primer extension. Quantitative PCR, which is also known as real-time PCR, involves the use of a reporter probe which typically has a fluorescence reporter or intercalating dye to enable quantitative detection in real time of the progress of the PCR reaction.

Where kits for the synthesis or amplification of a target nucleic acid sequence including PCR and quantitative PCR kits are provided in accordance with the invention the active nucleic acid polymerase and the non-functional mutant nucleic acid polymerase protein may be provided in separate containers or may be provided mixed together as a stabilized composition. Optionally, instructions for performing the method such as PCR or qPCR are provided in the kits. Such instructions may be provided as a packaging insert, on the packaging itself or encoded on digital media with the kit or remote therefrom.

The present invention will now be described in further detail by way of example only, with reference to the accompanying drawings.

DESCRIPTION OF THE DRAWINGS

FIG. 6. (Example 5)
control—Taq DNA polymerase stock solution (with non-ionic polymeric detergents); Taq:BSA (w/w)—Taq DNA polymerase mixture with BSA at indicated weight ratios without non-ionic polymeric detergents).

FIG. 7A-J. (Example 6)
A-J: Template-primer concentration—1 nM
Protein concentrations—0, 1, 2, 5, 10, 20, 50, 100, 200, 500, 1000 nM FIG. 8A-J. (Example 6)
A-J:
Primer concentration—1 nM
Protein concentrations—0, 1, 2, 5, 10, 20, 50, 100, 200, 500, 1000 nM
FIG. 9A-B. (Example 6)
A; B: K—Taq DNA polymerase (5 u/mkl-~70 ng/mkl); 1—adsorbed Taq DNA polymerase; 2—Taq DNA polymerase in solution.
FIG. 11A-D. (Example 8)
A-D: 1, 2, 3, 4—0.1, 1, 10, 100 ng human DNA/50 mkl, respectively
FIG. 12A-D. (Example 9)
A-D: 1, 2, 3, 4, 5—0.01, 0.1, 1, 10, 100 ng human DNA/50 mkl, respectively
FIG. 13. (Example 10)
Stock solutions: Taq DNA polymerase (5 u/mkl)+:
1. non-ionic polymeric detergent;
2—12 inactive Taq DNA polymerase mutants (2.8 mkg/mkl):
2—H540C/D610A/H784C; 3—R536C/H540C/D610A/H784C; 4—N485S/R536C/H540C/H784C;
5—I532T/R536C/H540C/H784C; 6—(H540C/H784C)/(Y81F/G187A); 7—(H540C/H784C)/(R25S/Y81F);
8—(H540C/H784C)/(R25S/G187A); 9—(H540C/H784C)/(R25S/Y81F/G187A);
10—(I532T/R536C/H540C/H784C/)/(Y81F/G187A);
11—(R536/H540C/D610A/H784C/)/(Y81F/G187A);
12—(I532T/R536C/H540C/H784C/)/(R25S/Y81F/G187A).

FIG. 21A-D. (Example 18)
A, B—mouse ear tissue lysate; C, D—mouse tail tissue lysate;
A, C—1 mkl tissue lisate; B, D—4 mkl tissue lisate;
A-D: Maxima Hot Start Green PCR Master Mix (1×):
1—without additional protein;
2, 3—+BSA (300 ng and 600 ng/mkl, respectively);
5, 6—+(R536C/K540C/D610A/H784C)/(Y81F/G187A) (50 ng and 150 ng/mkl, respectively).

DETAILED DESCRIPTION OF INVENTION

Example 1. Adhesion of Taq DNA Polymerase onto Hydrophobic Surfaces

Recombinant Taq DNA polymerase was purified without the addition of any detergent in any step. Fractions containing the enzyme were pooled and dialyzed against storage buffer without non-ionic polymeric detergents (20 mM Tris-HCl, pH 8.0 at 25° C.; 100 mM KCl, 1 mM DTT, 0.1 mM EDTA, 50% (v/v) glycerol). Enzyme concentration was estimated using Bradford Reagent (Fermentas) following manufacturer's recommendations. The DNA polymerase and 5'-3' exonuclease activity assays were performed by measuring incorporation of [methyl-$^3$H]-dTTP into polynucleotide fraction or degradation of [$^3$H]-labelled polynucleotide.

Preliminary assessment of Taq DNA polymerase stability in solutions with and without detergents was performed using two concentrations of enzyme (~70 ng/mkl ("lower concentration") and ~350 ng/mkl ("higher concentration"), which corresponded respectively to 5 u/mkl and 25 u/mkl activity of Taq DNA polymerase). Four tubes each containing 100 μl of stock solutions of Taq DNA polymerase in the two above indicated concentrations were prepared using storage buffer with or without non-ionic polymeric detergents (0.5% (v/v) Nonidet P40 and 0.5% (v/v) Tween 20) in 1.5 ml standard Eppendorf type test tubes.

Figure 1A:
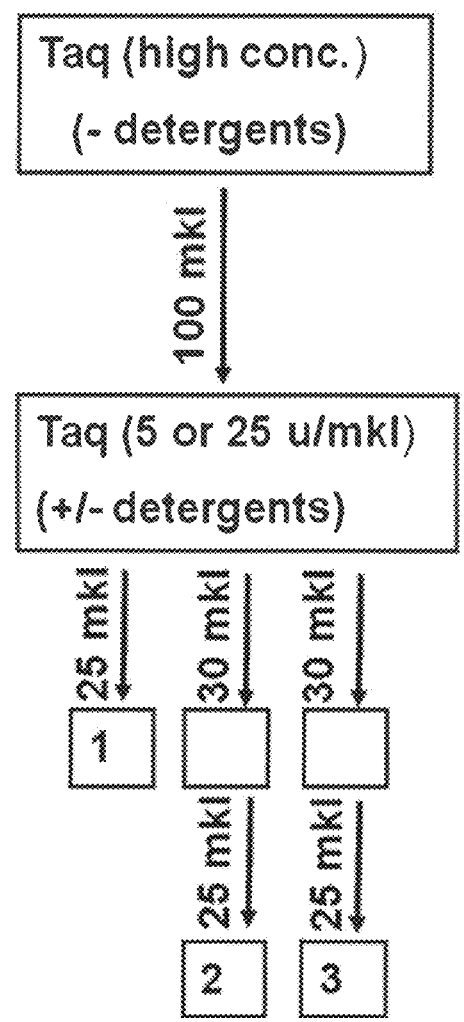
FIG. 1A-C. (Example 1)
A-C: 1—Taq DNA polymerase stock solution; 2—Taq DNA polymerase after transfer into new tube and centrifugation; 3—Taq DNA polymerase after heating and centrifugation.

Each stock solution was further dispensed into three 1.5 ml tubes by adding 25 mkl into one tube and 30 mkl into the other two tubes. The first tube with 25 mkl of Taq stock solution was used as control when estimating amount of Taq DNA polymerase in the stock solution (No1). The second tube with 30 mkl was centrifuged for 5 minutes at 16.000 g to sediment all aggregated insoluble proteins and 25 mkl of the supernatant were transferred to another 1.5 ml tube (No2). The third tube with 30 mkl was heated for 180 min at 80° C., centrifuged for 5 min at 16.000 g and 25 mkl of the supernatant were transferred to the tube No3. Experimental scheme is presented in FIG. 1A.

After the experiment, 10 μl of 5× Loading buffer (Fermentas), 2.5 mkl of 20×DTT and 12.5 mkl of miliQ water were added to all six tubes with 25 mkl of Taq DNA polymerase solutions of lower concentration (initial concentration was ~70 ng/mkl) to yield final volume of 50 mkl. In parallel, 50 μl of 5× Loading buffer, 6.25 mkl of 20×DTT and 68.75 mkl miliQ water were added to all six tubes with 25 mkl of Taq DNA polymerase solutions of higher concentration (initial concentration was ~350 ng/mkl) to yield final volume of 125 mkl. The samples were heated for 10 min at 95° C., cooled, then 10 mkl from the tubes with lower enzyme concentration and 5 mkl from the tubes with higher enzyme concentration were loaded onto 10% SDS-PAAG gel (total normalized amount of the enzyme in all lanes was ~350 ng, calculating from initial stock concentrations). The PageRuler™ Prestained Protein Ladder (Fermentas) was used as a marker. After electrophoresis the gels (FIG. 1B, 1C) were analyzed by Ultra Lum Electronic U.V. Transilluminator (Ultra-Lum) and Totallab™ TL-100 version 2006[b] Software (Nonlinear dynamics Ltd.) (FIG. 2B, C).

Figures 1B, 1C:
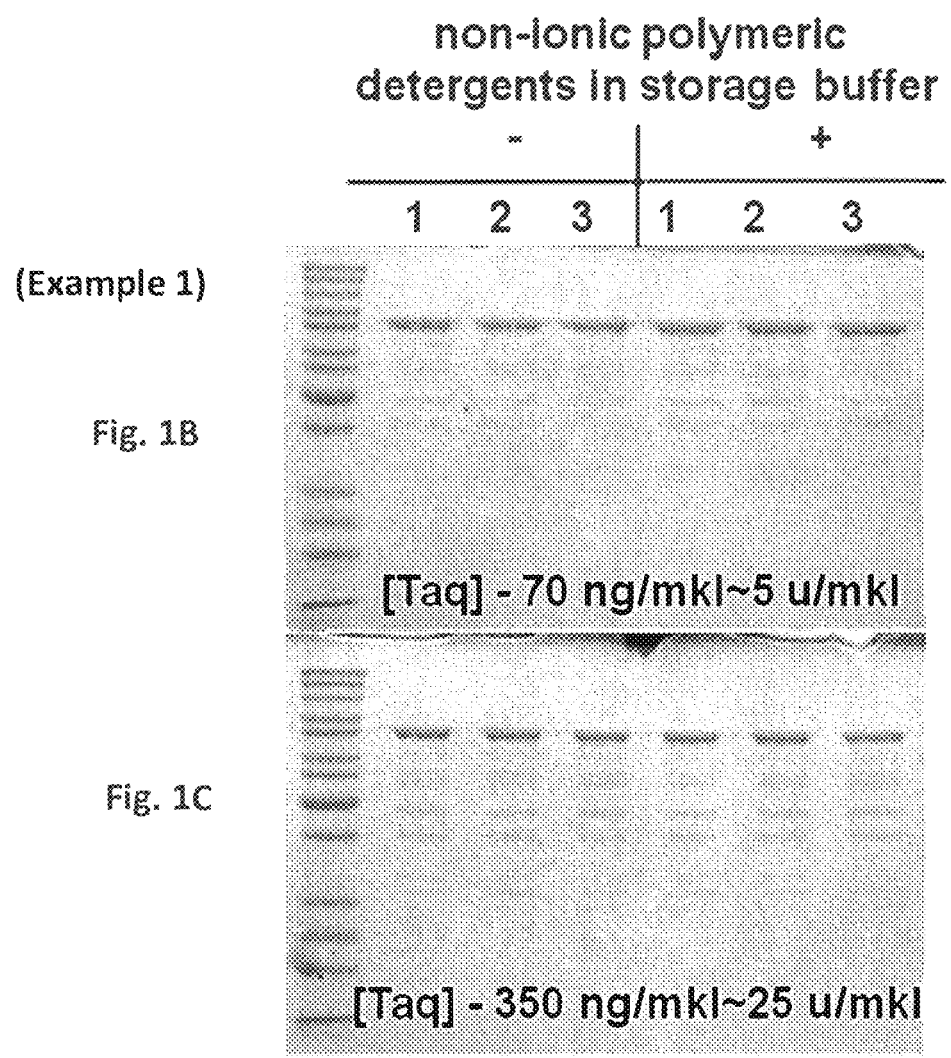

SDS gel analysis revealed that low concentration Taq DNA polymerase preparations (5 u/mkl) with no detergents in the buffer solution retained only 80% of polymerase protein found in the respective preparations of Taq DNA polymerase with detergents (FIG. 1B, Table 1). Heating of the samples that usually prevents enzyme loss and increases protein solubility in cases of protein aggregation had no positive effect on the actual concentration of Taq DNA polymerase prepared with no detergents if compared to the enzyme preparation of the same concentration stored in detergents containing buffer. Surprisingly, no such effect was observed when 5-time higher enzyme concentrations were used for comparison (FIG. 1C, Table 1). Based on these results we presume that lower actual concentrations of Taq DNA polymerase observed in the absence of non-ionic polymeric detergents were caused by enzyme adhesion on hydrophobic surface of the tube used for preparing enzyme stock solution. Hence, tested higher enzyme concentrations were above sorption saturation level as well as below the lowest limit of method sensitivity and, therefore, were undetectable.

It is known in the art that enzyme adsorption on the hydrophobic supports may strongly alter enzyme conformation thereby inhibiting their enzymatic activities (Noinville et al. (2002) *Biopolymers* 67:323-326). Previously it was shown that Taq DNA polymerase can be effectively adsorbed on different microfluidic materials (Prakash et al. (2008) *Microfluid. Nanofluid.* 4: 295-305). Wang et al have demonstrated that adsorption of Taq DNA polymerase (not the nucleic acid) on the silicon-related material surface was the primary cause of reaction inhibition phenomenon and that silicon did not participate directly in the amplification process (Wang et al. (2006) *J. Biomed. Mater. Res. A.* 77: 28-34).

TABLE 1

Amount of Taq DNA polymerase retained in soluble form in solutions with or without detergents.

| Sample No | Soluble fraction of the enzyme (5 u/mkl) | | Soluble fraction of the enzyme (25 u/mkl) | |
|---|---|---|---|---|
| | in the presence of detergents (%) | in the absence of detergents (%) | in the presence of detergents (%) | in the absence detergents (%) |
| 1 | 100 | ~80 | 100 | ~100 |
| 2 | ~100 | ~80 | ~100 | ~100 |
| 3 | ~100 | ~80 | ~100 | ~100 |

1- Taq DNA polymerase in the initial stock solution;
2- Taq DNA polymerase after transfer into new tube and centrifugation (5 min at 16.000 g);
3- Taq DNA polymerase after heating (180 min. at 80° C.) and centrifugation (5 min at 16.000 g).

Example 2: Adsorption of Taq DNA Polymerase in Different Micro Test Tubes

To confirm that adhesion plays key role in the loss of functionality of the Taq DNA polymerase, model experiments with Taq DNA polymerase were performed with different widely used plastic microassay tubes (1.5 ml micro vial, 0.5 ml PCR micro tube, 0.2 ml PCR micro tube) by transferring enzyme preparation sequentially though several tubes.

Figure 2A:
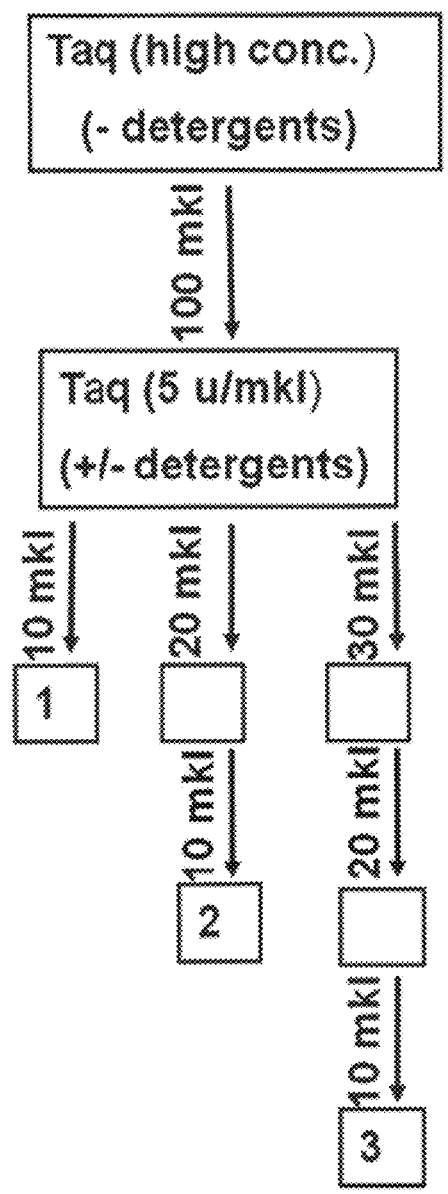
FIG. 2A-D. (Example 2)
A; B: 1—Taq DNA polymerase stock solution; 2—Taq DNA polymerase after transfer into the first 1.5 ml tube; 3—Taq DNA polymerase after transfer into the second 1.5 ml tube;
C: 4—Taq DNA polymerase stock solution; 5—Taq DNA polymerase after change one 0.2 ml PCR micro tube; 6—Taq DNA pol. after changes two 0.2 ml PCR micro tubes.
D: 7—Taq DNA pol. in total storage solution; 8—Taq DNA pol. after change one 0.5 ml PCR micro tube; 9—Taq DNA pol. after changes two 0.5 ml PCR micro tubes.
Figure 2B:
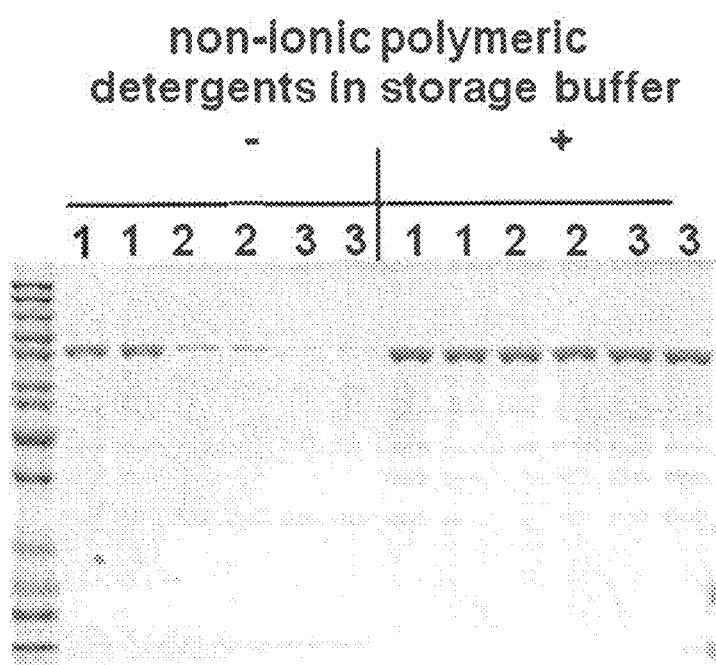

Stock solutions of Taq DNA polymerase in high and low concentration (~70 ng/mkl; 5 u/mkl) prepared in the absence or presence of non-ionic polymeric detergents were dispensed into 1.5 ml standard Eppendorf type micro test tubes as described in Example 1. Further on prepared stock solutions were dispensed into three 1.5 ml tubes, containing 10 mkl, 20 mkl and 30 mkl of stock solution, respectively. The first tube with 10 mkl was used as control when estimating amount of Taq DNA polymerase in the stock solution (No1). The second tube with 20 mkl was incubated at room temperature for 1 hour mixing it during the incubation 3 times for 5 seconds and, after centrifugation, 10 mkl were transferred to the new test tube No2. The third tube with 30 mkl was incubated at room temperature for 1 hour mixing it during the incubation 3 times for 5 seconds and, after centrifugation, 20 mkl were transferred to the new 1.5 ml micro test tube. The resulting 20 mkl sample was further incubated for 1 hour mixing it 3-times for 5 seconds and, after centrifugation, 10 mkl were again transferred to the new test tube No3. The preparation of samples is schematically shown in FIG. 2A.

After experiment 3 µl of 5× Loading buffer, 0.75 mkl of 20×DTT and 1.25 mkl miliQ water were added to all test tubes with 10 mkl Taq DNA polymerase solutions (No 1, 2, 3) resulting in the total sample volume of 15 mkl. The samples were heated at 95° C. for 10 min, cooled, and 5 mkl of each sample (which corresponds to total amount of the enzyme of ~230 ng, calculating from the initial concentration) were assayed by SDS-PAAG gel electrophoresis (FIG. 2B).

Figures 2C, 2D:
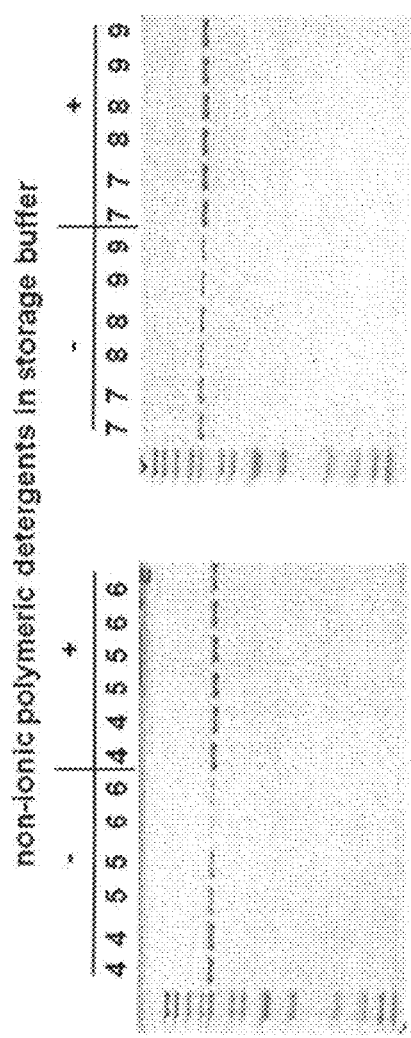

Analogous experiments with other plastic tubes were performed in a similar manner as described above and schematically are presented in FIG. 2A, except that 0.2 ml and 0.5 ml PCR micro test tubes were used instead of 1.5 ml standard Eppendorf type tubes and numbering of the samples was 4, 5, 6 in the case of 0.2 ml PCR tube and 7, 8, 9 in the case of 0.5 ml PCR tube (FIG. 2C, D).

SDS gel analysis revealed that amount of Taq DNA polymerase retained in the solution in the absence of detergents decreased during each enzyme transfer into the next test tube and was equal respectively to ~70%, ~20% and ~10% as compared to that of Taq DNA polymerase preparation with detergents sequentially transferred in the same manner through three 1.5 ml micro test tubes (FIG. 2B, Table 2.1).

Similar experiments performed with micro test tubes of other types revealed that each kind of tested tube exhibits protein binding properties and efficiency of adsorption depends not only on the surface area of the tube that contacts with the enzyme, but also on the origin of polymeric material used for tube casting: the fraction of Taq DNA polymerase retained in solution after passage through a set of 0.2 ml PCR test tubes was lower if compared with that in case when 0.5 ml PCR test tubes were used (see FIG. 2C, 2D and Tables 2.2 and 2.3, respectively).

TABLE 2.1

Soluble fraction of Taq DNA polymerase retained after sequential enzyme passage through 1.5 ml micro test tubes.

| Sample No | Soluble fraction of Taq DNA pol. in the presence of detergents (%) | Soluble fraction of Taq DNA pol. in the absence of detergents (%) |
|---|---|---|
| 1 | 100 | ~70 |
| 2 | ~100 | ~20 |
| 3 | ~100 | ~10 |

1- Taq DNA polymerase in stock solution;
2- Taq DNA polymerase after first transfer into 1.5 ml tube;
3- Taq DNA polymerase after second transfer into 1.5 ml tube.

TABLE 2.2

Soluble fraction of Taq DNA polymerase retained after sequential enzyme passage through 0.2 ml PCR micro tubes.

| Sample No | Soluble fraction of Taq DNA pol. in the presence of detergents (%) | Soluble fraction of Taq DNA pol. in the absence of detergents (%) |
|---|---|---|
| 4 | 100 | ~90 |
| 5 | ~100 | ~50 |
| 6 | ~90 | ~20 |

4- Taq DNA polymerase in stock solution;
5- Taq DNA polymerase after first transfer into 0.2 ml PCR tube;
6- Taq DNA polymerase after second transfer into 0.2 ml PCR tube.

TABLE 2.3

Soluble fraction of Taq DNA polymerase retained after sequential enzyme passage through 0.5 ml PCR micro tubes.

| Sample No | Soluble fraction of Taq DNA pol. in the presence of detergents (%) | Soluble fraction of Taq DNA pol. in the absence of detergents (%) |
|---|---|---|
| 7 | 100 | ~90 |
| 8 | ~100 | ~70 |
| 9 | ~100 | ~50 |

7- Taq DNA polymerase in stock solution;
8- Taq DNA polymerase after first transfer into 0.5 ml PCR tube;
9- Taq DNA polymerase after second transfer into 0.5 ml PCR tube.

Example 3: Adsorption of Taq DNA Polymerase on the Surface of Different Micro Test Tubes Direct physical evidence that Taq DNA polymerase is adsorbed on the surface of different test tubes was obtained by eluting adsorbed enzyme from the surface of plastic tubes with SDS solution.

Stock solutions of Taq DNA polymerase (~70 ng/mkl; 5 u/mkl) prepared in the absence or presence of non-ionic polymeric detergents were dispensed into different micro test tubes (1.5 ml micro tube, 1.5 ml storage micro tube, 0.5 ml PCR micro tube) as described in Example 1, except that total volumes of stock solution were 20 mkl instead of 100 mkl.

Prepared samples were incubated at room temperature for 1 hour periodically mixing (3 times for 5 seconds in total). After centrifugation supernatants were removed and test tubes were washed 4-times with 40 mkl of storage buffer with no detergents to remove residual amounts of polymerase stock solution remaining in the tube. After a washing step 12 mkl of 1× Loading buffer (containing SDS) were added into empty test tubes and the samples were heated at 95° C. for 10 minutes. 9 mkl of supernatants obtained after centrifugation were mixed with 3 mkl of 4× Loading buffer (Fermentas). Control samples with known protein amount (K) were prepared by mixing of 5 mkl of commercial Taq DNA polymerase with 3 mkl 4× Loading buffer. The 5 mkl of each sample were analyzed by SDS-PAA gel electrophoresis (FIG. 2B).

TABLE 3

Figures 3A, 3B, 3C:
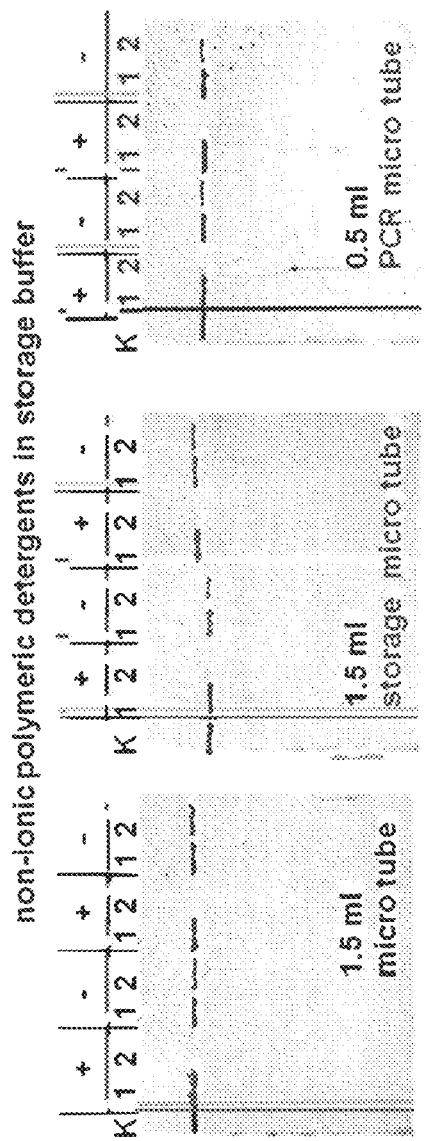
FIG. 3A-C. (Example 3)
A-C: K—Taq DNA polymerase commercial preparation (5 u/mkl-~70 ng/mkl); 1—Taq DNA polymerase in solution; 2—adsorbed Taq DNA polymerase.

Adhesion of Taq DNA polymerase in different micro test tubes. SDS gel analysis revealed that 1.5 ml micro tube, 1.5 ml storage micro tube, 0.5 ml PCR micro tube adsorbed ~560 ng, ~430 ng and ~300 ng Taq DNA polymerase, respectively (FIG. 3A-3C); Table 3).

| Sample No | Adsorbed amount of Taq DNA pol. (ng) | Adsorbed activity of Taq DNA pol. (units) |
|---|---|---|
| 1 | ~560 | ~40 |
| 2 | ~430 | ~31 |
| 3 | ~300 | ~21 |

1- adhesion of Taq DNA polymerase in 1.5 ml micro tube;
2- adhesion of Taq DNA polymerase in 1.5 ml storage micro tube;
3- adhesion of Taq DNA polymerase in 0.5 ml PCR micro tube.

Example 4: Efficiency of PCR Using Excess of Taq DNA Polymerase

Experimental data indicate that test tubes, including 0.5 ml PCR micro tubes, adsorb fixed amount of Taq DNA polymerase (Table 3), therefore, it is feasible to presume that when excess amounts of Taq DNA polymerase are used in the absence of detergents in the reaction mixture the enzyme should absorb onto tube surface up to saturation and the remaining enzyme in the solution should generate the PCR product. The experiments to test this presumption were performed using set of PCR primers (for amplification CFTR gene fragment) and human genome DNA as a template.

Figure 4:
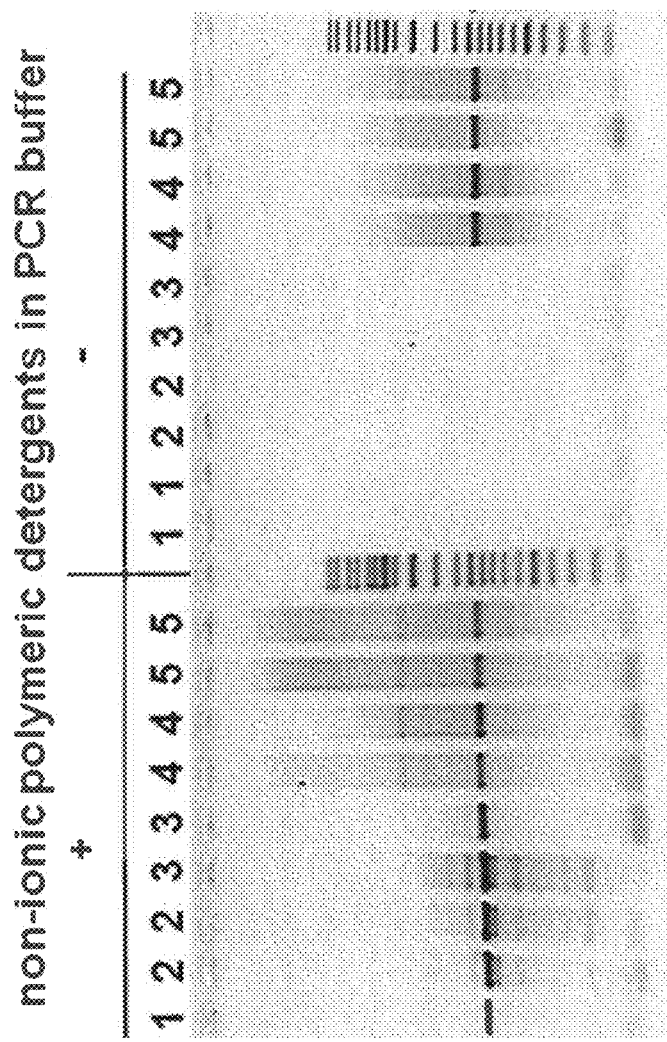
FIG. 4. (Example 4)
1, 2, 3, 4, 5—1.25, 6.25, 12.5, 50, 75 u/50 mkl of Taq DNA polymerase, respectively FIG. 5. (Example 5)
control—Taq DNA polymerase stock solution (with non-ionic polymeric detergents); Taq:BSA (w/w)—Taq DNA polymerase mixture with BSA at indicated weight ratios without non-ionic polymeric detergents. 1—Taq DNA polymerase stock solution; 2—Taq DNA polymerase after the transfer into the second 1.5 ml tube.

PCR was carried out in the Mastercycler (Eppendorf). The amplification reactions were performed using 1.25, 6.25, 12.5, 50, 75 units of Taq DNA polymerase in 50 mkl 1× reaction buffer (10×: 750 mM Tris-HCl, pH8.8 at 25° C.; 200 mM $(NH_4)_2SO_4$) in the absence or presence of 0.01% (v/v) Tween 20. Both buffers were supplemented with 2 mM $MgCl_2$. 0.2 mM dNTP, 0.5 mkM of each PCR primer and human DNA (100 ng/50 mkl). A 950 bp DNA fragment of CFTR gene was amplified with the following set of PCR primers: 5'-GCTGCATCATATAAGTTGCC-3' and 5'-AAGGCTACACTGTTAATTTT-3'. Components of PCR reaction were mixed at room temperature and reactions were performed using the following cycling profiles: 95° C.—3 min; (95° C.—0.5 min, 50° C.—0.5 min, 72° C.—1 min)—35 cycles; 72° C.—5 min. After reaction the samples were mixed with aliquots (10 μl) of the 6× MassRuler™ Loading Dye (Fermentas), and the samples were analyzed by gel electrophoresis in 0.7% agarose. The GeneRuler™ DNA Ladder Mix (Fermentas) was used for evaluation of the amplicon size. Electrophoresis was performed in the 1×TBE buffer (89 mM Tris, 89 mM $H_3BO_3$, and 1 mM EDTA) at 5 V/cm for 75 min. After completion of electrophoresis, gels were stained with ethidium bromide (0.5 μg/ml) and destained afterwards in MiliQ-quality water for 20 minutes. After electrophoresis DNA bands were visualized by Ultra Lum Electronic U.V. Transilluminator (Ultra-Lum) (FIG. 4).

The PCR experiments confirmed our presumptions. PCR products were obtained in the excess of enzyme (50 u/50 mkl, 75 u/50 mkl) in the absence of detergents (FIG. 4). These data quite well correlate with estimated adsorbed amounts of Taq DNA polymerase (Table 3). However, practical uses of the excess amounts of the DNA polymerase have at least two disadvantages:

a. PCR products quality and yield varies depending on the plastic type (and other reaction components such as template DNA, primers) used for certain experiment;

b. process is difficult to control in different systems, therefore results are inconsistent.

Example 5: Effect of Inert Proteins on Taq DNA Polymerase Functionality in Solutions without Detergents Bovine serum albumin (BSA) is routinely used to enhance the stability of proteins during storage or in biological assays and to prevent adhesion of the enzyme to micro test tubes. Also, U.S. Pat. No. 5,284,940 teaches the use of transferrin, globin, or serum albumin to neutralize the activity of polymerase inhibitors during amplification reaction. The experiments were performed as described in Example 3, except that stock solutions of Taq DNA polymerase without detergents in low and high concentration (~70 ng/mkl; 5 u/mkl) were prepared using increasing BSA concentrations (Fermentas) at weight ratios: 1:0, 1:1, 1:5, 1:10, 1:15, 1:20 (FIG. 5) and analyzed by SDS PAAGE.

The second set of experiments was performed as described above, except that the stock solutions of Taq DNA polymerase (~70 ng/mkl; 5 u/mkl) without detergents were prepared using increasing concentrations of BSA, at weight ratios: 1:0, 1:1, 1:5, 1:10, 1:20, 1:40 and used for PCR reactions. Amplification reactions were performed using 1.25 units of Taq DNA polymerase from the prepared mixtures with BSA in 50 mkl reaction buffer (FIG. 6).

SDS gel analysis revealed that soluble fraction of Taq DNA polymerase increased concurrently with increased BSA concentration (FIG. 5, Table 4), however, in all cases PCR products were obtained only when non-ionic polymeric detergents were added to reaction buffer despite various Taq DNA polymerase/BSA ratios used in experiments (FIG. 6). Starting with Taq:BSA 1:5 w/w ratios consistent and similar yields of PCR product were observed, indicating that similar effective amounts of Taq DNA polymerase were added to PCR mixture from stock solutions. Absence of specific PCR product in the reaction mixtures with no non-ionic polymeric detergents (FIG. 6) indicate that BSA (at used concentrations) is not the best candidate protein to prevent enzyme sorption to the test tubes during reaction.

TABLE 4

Soluble fraction of Taq DNA polymerase in the presence of BSA

| Sample | | Soluble fraction of Taq DNA pol. (%) |
|---|---|---|
| control | | 100 |
| Taq:BSA 1:0 | 1 | ~70 |
| | 2 | ~20 |
| Taq:BSA 1:1 | 1 | ~70 |
| | 2 | ~20 |
| Taq:BSA 1:5 | 1 | ~70 |
| | 2 | ~50 |
| Taq:BSA 1:10 | 1 | ~70 |
| | 2 | ~60 |
| Taq:BSA | 1 | ~70 |

TABLE 4-continued

Soluble fraction of Taq DNA polymerase in the presence of BSA

| Sample | | Soluble fraction of Taq DNA pol. (%) |
|---|---|---|
| 1:15 | 2 | ~70 |
| Taq:BSA 1:20 | 1 | ~70 |
| | 2 | ~70 | control - Taq DNA polymerase (with non-ionic polymeric detergents in the storage buffer),
Taq:BSA—Taq DNA polymerase mixture with BSA (at indicated weight ratios) in the storage buffer with no detergents.
1- Taq DNA pol. in stock solution;
2- Taq DNA polymerase after passage through two 1.5 ml test tubes.

Practical uses of native BSA as stabilizer have certain disadvantages similarly to all other products of animal origin. Uses of products of animal origin in diagnostics and other biotechnology applications are often not acceptable due to possible contamination of products with animal DNA, animal viruses or other infection agents such as prions and especially the possibility of contamination with infectious agents that have not been yet discovered.

Although international patent application WO/2007/123689A1 (New England BioLabs) discloses expression, secretion and purification of recombinant bovine serum albumin (rBSA) and uses thereof including the stabilization of some enzymes, BSA is not a thermophilic protein, so thermal cycling can denature the protein during reaction thereby negatively affecting its action as stabilizer. This phenomenon could account for the failure of BSA to prevent Taq DNA polymerase sorption to the tube during the PCR reactions in our experiments.

Figure 5:
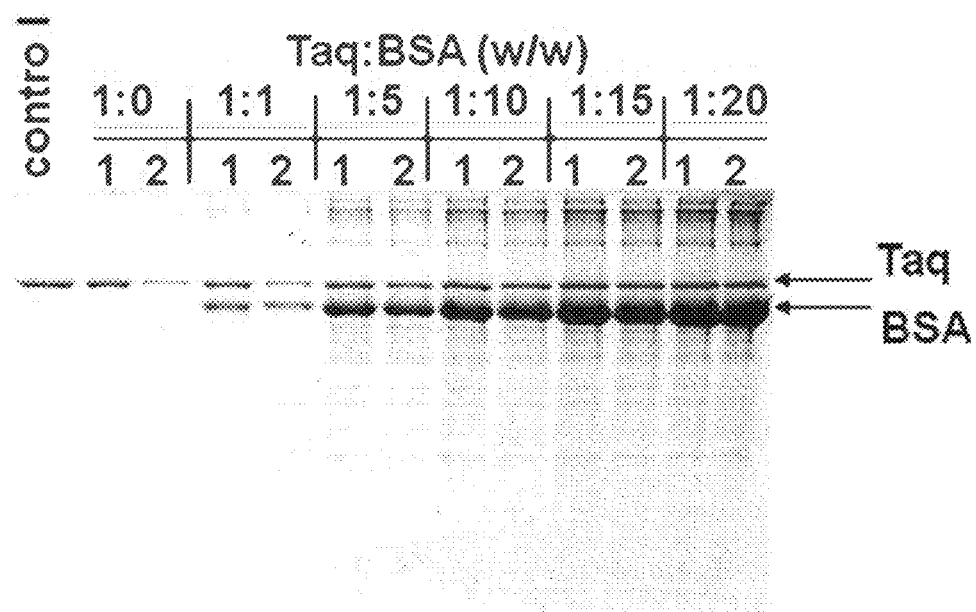
Figures 7A, 7B:
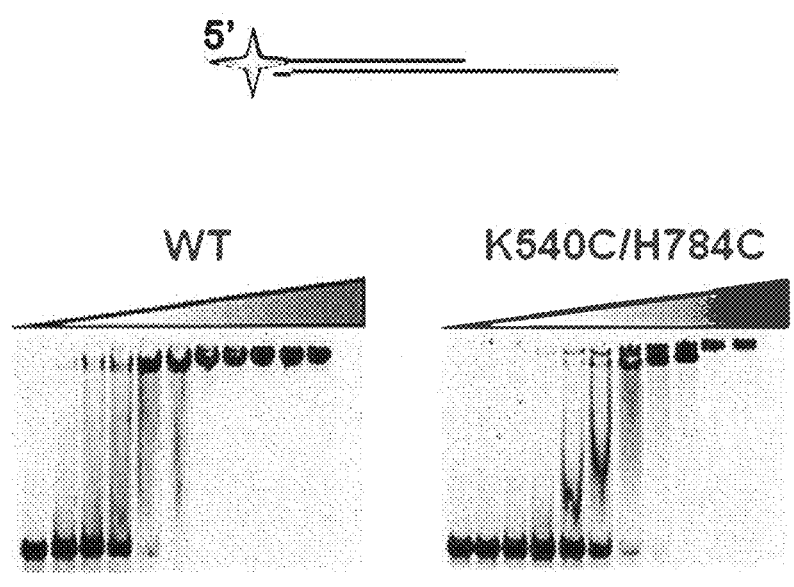
Figures 7C, 7D:
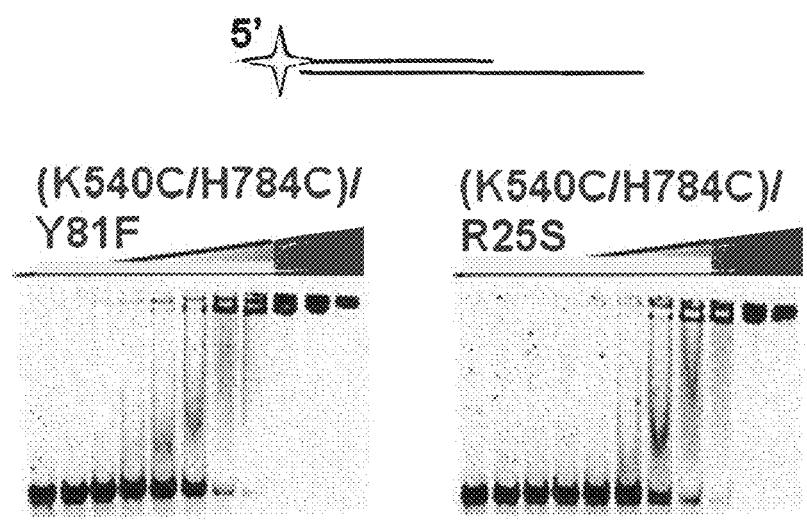
Figure 7G:
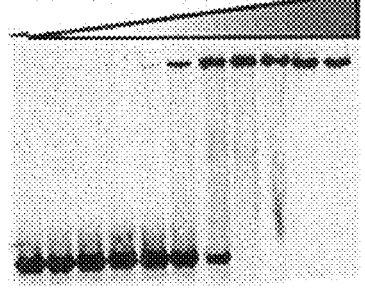
Figure 7H:
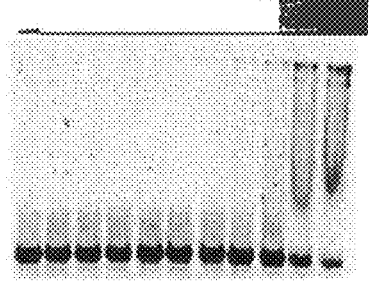

Example 6: Construction of Non-Functional Taq DNA Polymerase Mutants and Analysis of Their Properties Experimental data suggest that adhesion of Taq DNA polymerase to the surface of test tubes during storage without detergents (Tables 1, 2.1, 2.2, 2.3, 3) is one of the main reasons for non-functionality of the enzyme in reaction mixtures. The problem was partly solved using excess amounts of polymerase (FIG. 4) or using another protein competitive for adsorption such as BSA (FIG. 5, 6). However each of the indicated approaches has certain drawbacks as presented above.

We propose to solve the problem of DNA polymerase adhesion to tube surfaces during storage and reactions using inert thermophilic protein that:

1. is deficient in catalysis and substrate binding (e.g. non-functional mutant of the same polymerase);
2. has similar physical properties to those of wild-type polymerase, including thermostability and enzyme surface hydrophobicity.

To test this suggested approach point mutants of Taq DNA polymerase were constructed. Target amino acids for polymerase active site mutagenesis (R536, K540, D610 and H784) were chosen based on Taq DNA polymerase 3D analysis (Eom et al. (1996) Nature 328: 278-281), while targets for 5'-3' exonuclease active site mutagenesis (R25, Y81 and G187) were chosen based on primary sequence homology and mutagenesis results (Ishino et al. (1995) Protein Engineering 8: 1171-1175; Riggs et al. (1996) Biochim. Biophys. Acta 1307: 178-186). Mutations in E491, N485, I532 positions were obtained incidentally, most likely, as a result of incorrect primer sequence or missincorporation of nucleotides during PCR. The set of constructed Taq DNA polymerase mutants is presented in Table 5.

TABLE 5

Taq DNA polymerase mutants.

| polymerase active site mutation | 5'-3' exonclease active site mutation | Polymerase activity (%) | 5'-3' exonclease activity (%) |
|---|---|---|---|
| — | — | 100 | 100 |
| K540C/H784C | — | 11 | 100 |
| K540C/D610A/H784C | — | ~0* | 55 |
| R536C/K540C/D610A/H784C | — | 1 | 15 |
| E491G/R536C/K540C/H784C | — | 3 | 12 |
| N485S/R536C/K540C/H784C | — | 1 | 12 |
| I532T/R536C/K540C/H784C | — | ~0* | 10 |
| K540C/H784C | R25S | 14 | 5 |
| K540C/H784C | Y81F | 13 | 9 |
| K540C/H784C | R25S/Y81F | 8 | ~0* |
| K540C/H784C | R25S/G187A | 7 | 1 |
| K540C/H784C | Y81F/G187A | 6 | ~0* |
| K540C/H784C | R25S/Y81F/G187A | 9 | ~0* |
| R536C/K540C/D610A/H784C | Y81F/G187A | ~0* | ~0* |
| I532T/R536C/K540C/H784C | Y81F/G187A | 1 | ~0* |
| I532T/R536C/K540C/H784C | R25S/Y81F/G187A | ~0* | ~0* |

*estimated activity was less than 0.5%.

Site-directed mutagenesis was performed by the megaprimer method (Barik. (1995) *Mol. Biotechnol.* 3: 1-7) using pair of primers flanking the polymerase gene and oligonucleotides encoding desired mutations. Obtained PCR products were cloned into prepared vector. Presence of required mutations, as well as the absence of additional mutations was confirmed by sequencing. Taq DNA polymerase mutants were purified without addition of any non-ionic polymeric detergents. Fractions containing the enzyme were pooled and dialyzed against storage buffer without non-ionic polymeric detergents (20 mM Tris-HCl (pH 8.0 at 25° C.), 100 mM KCl, 1 mM DTT, 0.1 mM EDTA, 50% (v/v) glycerol). Concentrations of mutant enzymes were estimated using Bradford Reagent (Fermentas) as recommended by the manufacturer.

All mutants were assayed for DNA polymerase and 5'-3' exonuclease activity. DNA polymerase and 5'-3' exonuclease activity assays were performed by measuring incorporation of [methyl-$^3$H]-dTTP into polynucleotide fraction or degradation of [$^3$H]-labelled polynucleotide. Obtained data confirmed that mutagenesis of polymerase and 5'-3 exonuclease active sites resulted in reduced/inactivated polymerase and nuclease activities.

DNA binding properties of Taq DNA polymerase mutants were investigated using electrophoretic mobility shift assay (EMSA).

Affinity of Taq DNA polymerase (FIG. 7A) and its mutants (FIG. 7B-J) for double-stranded DNA (template-primer duplex) was analyzed by electrophoretic mobility shift assays (EMSA) as previously described (Lagunavicius et al. (2003) *J. Mol. Biol.* 326: 1051-1064) except that 1 nM of 24*/44 nt duplex (* indicates $^{33}$P label in 5'-terminus of 24 nt oligonucleotide) formed by annealing of 5'-TTT-TAGCCGCTAGAGTCGACCTGC-3' (24 nt) and 5'-GGA-GACAAGCTTGTATGCCTGCAGGTCGACTCTAGCG-GCTAAAA-3' (44 nt) and 0, 1, 2, 5, 10, 20, 50, 100, 200, 500, 1000 nM of the proteins were mixed in 1×TAE buffer (40 mM Tris-acetate, pH8.3 at 25° C.; 2 mM EDTA) supplemented with 10% glycerol and electrophoresis was performed in 12% PAAG. The gels were analyzed by Cyclone Storage Phosphor System and OptiQuant™ Image Analysis Software (Packard Instruments) and GraphPad Prism version 4.03 Software (GraphPad Software, Inc.) (FIG. 7).

Figures 8A, 8B:
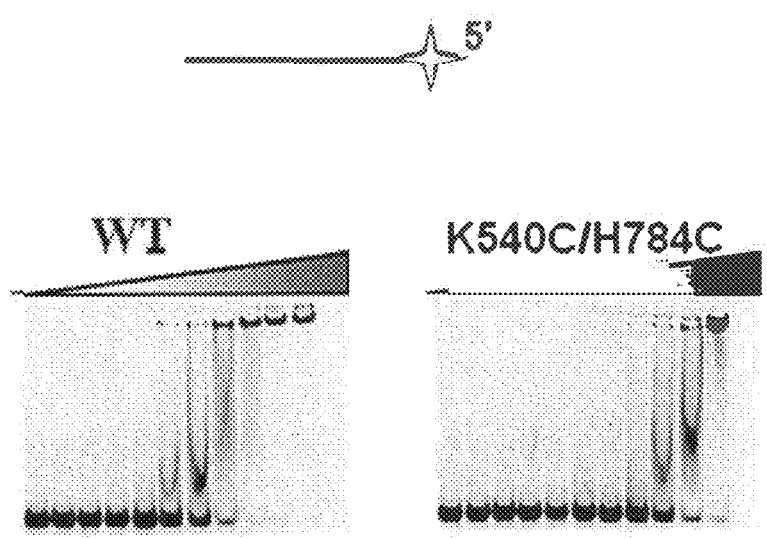
Figures 8C, 8D:
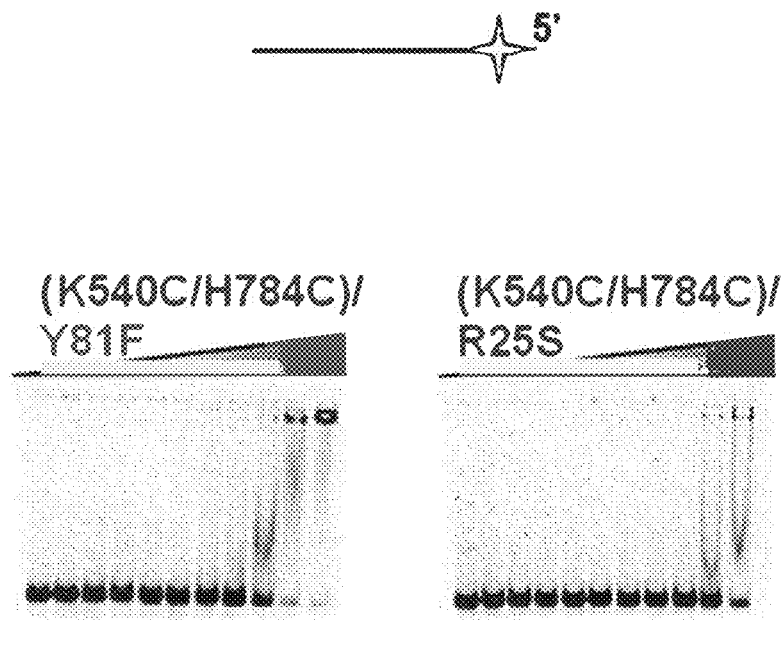
Figures 8G, 8H:
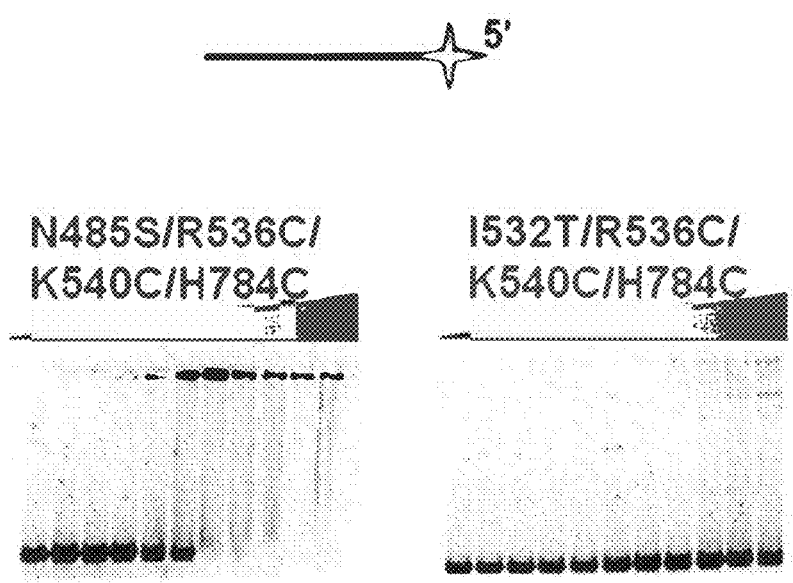

Affinity of Taq DNA polymerase (FIG. 8A) and its mutants (FIG. 8B-G) for single-stranded DNA (primer) was analyzed as described in Example 7, except that 5'-labeled 24 nt oligonucleotide (5'-TTTTAGCCGCTAGAGTCGAC-CTGC) was used instead of 24*/44 nt duplex (FIG. 8).

EMSA data show that majority of mutants have significantly lower affinities either for template-primer or primer substrates in comparison to WT Taq DNA polymerase (FIG. 7, 8). Summarized results of Taq DNA polymerase mutants affinity to DNA are presented in Table 6. These data indicate that catalytic mutants also have lower abilities to interact with primers and template-primer substrates during PCR.

TABLE 6

Affinity of Taq DNA polymerase mutants for DNA

| Taq DNA polymerase | Affinity for DNA ($K_d$, nM) | |
|---|---|---|
|  | Template-primer substrate | Primer |
| WT | 4.7 ± 1.6 | 79 ± 26 |
| K540C/H784C | 25 ± 8 | 460 ± 130 |
| (K540C/H784C)/Y81F | 28 ± 9 | 350 ± 120 |
| (K540C/H784C)/R25S | 56 ± 16 | 2700 ± 500 |
| R536C/K540C/D610A/H784C | 320 ± 100 | 2000 ± 200 |
| E491G/R536C/K540C/H784C | 200 ± 50 | 530 ± 100 |
| N485S/R536C/K540C/H784C | 32 ± 11 | 23 ± 7 |
| I532T/R536C/K540C/H784C | 990 ± 150 | 5200 ± 200 |
| (R536C/K540C/D610A/H784C)/(Y81F/G187A) | 2200 ± 600 | 3700 ± 400 |
| (I532T/R536C/K540C/H784C)/(R25S/Y81F/G187A) | 16000 ± 3000 | 7700 ± 400 |

To ensure that Taq DNA polymerase mutants have similar surface hydrophobicity and can be adsorbed on tube surface to similar levels in comparison to WT enzyme, we estimated adsorbed amounts of some mutant proteins by washing them from the surface of plastic tubes with SDS solution.

Figures 9A, 9B:
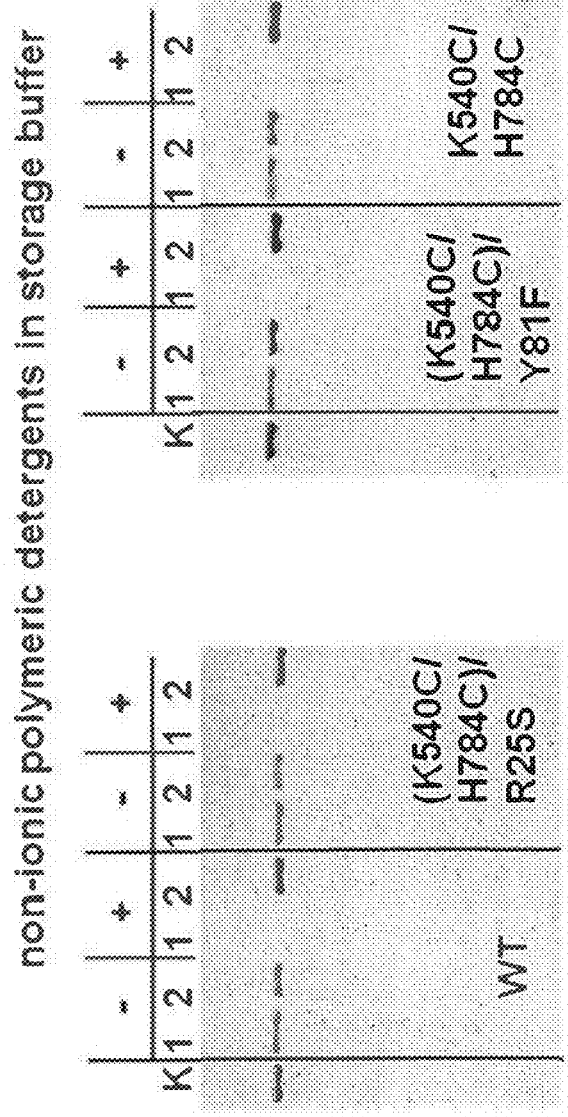

Experiments were performed in 1.5 ml micro test tubes as described in Example 3, except that enzyme mutants were used instead of WT Taq DNA polymerase (FIG. 9).

SDS gel analysis revealed that 1.5 ml test tubes adsorb similar amounts of Taq DNA polymerases mutants as compared with WT enzyme (FIG. 9; Table 7).

TABLE 7

Adsorbed amount of Taq DNA polymerase mutants.

| Taq DNA polymerase and its mutants | Adsorbed amount of enzyme (ng) |
|---|---|
| WT | ~580 |
| K540C/H784C | ~580 |
| K540C/H784C/Y81F | ~510 |
| K540C/H784C/R25S | ~650 |

Example 7. Effect of Non-Functional Taq DNA Polymerase Mutants on Taq DNA Polymerase Functionality in Solutions without Detergents We have tested the performance of Taq polymerase mixtures with inactive non-functional polymerases mutants added as stabilizers instead of detergents in the PCR reactions.

Initial PCR experiments were performed using mixtures of individually prepared Taq DNA polymerase and Taq DNA polymerase mutant (K540C/H784C) stock solutions, set of PCR primers (for amplification CFTR gene fragment) and human genome DNA as template in the presence or in the absence of non-ionic polymeric detergents.

Figure 10:
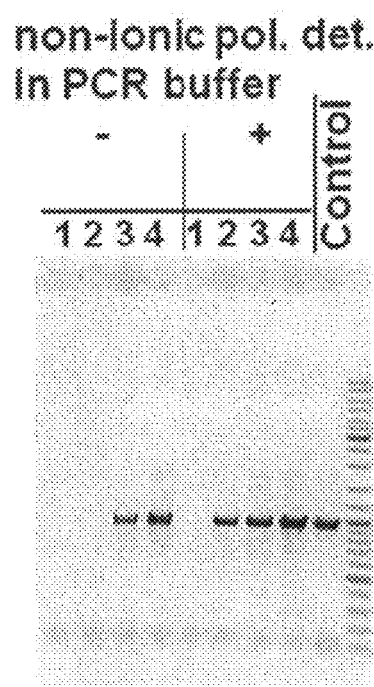
FIG. 10. (Example 7)
Control—1.25 u of commercial Taq DNA polymerase preparation in 50 mkl;
1, 2, 3, 4—700 ng K540C/H784C/50 mkl+0, 1.25, 2.5, 5 u Taq DNA polymerase/50 mkl, respectively.

The experiments were performed as described in Example 4, except that reactions were carried out using 0, 1.25, 2.5, 5 u Taq DNA polymerase and 700 ng of different inactive Taq DNA polymerase mutants in 50 mkl reaction buffer. The samples without Taq DNA polymerase were used to test residual activity of non functional Taq DNA polymerase mutants in the PCR. Commercial Taq DNA polymerase preparation was used as control (FIG. 10).

Experimental data clearly indicate that even large excess amounts of mutant enzymes alone did not generate PCR products, while Taq DNA polymerase mixtures with inactive mutant protein could synthesize PCR products both in the presence or absence of non-ionic polymeric detergents. However, addition of non-ionic polymeric detergents resulted in slightly higher yields of PCR products (FIG. 10).

Such results indicate that Taq DNA polymerase and non-functional mutants may be stored separately and added to reaction mixture directly before PCR reaction. Besides, PCR reaction using above described enzyme mixtures may be successfully performed without any surfactants like non-ionic polymeric detergents. Also our data allow for suggestion that Taq DNA polymerase may be stably stored in the presence of excess amounts of non-functional mutants of the same polymerase.

Example 8: PCR Using Different Storage Compositions of Taq DNA Polymerase with Non-Functional Mutant Detailed studies to identify optimal stable composition of Taq DNA polymerase suitable for long term storage were performed using all three inactive mutants and different Taq DNA polymerase/mutant ratios. Reactions were carried out in the presence or in the absence of non-ionic polymeric detergents in the reaction buffer.

Figure 11B:
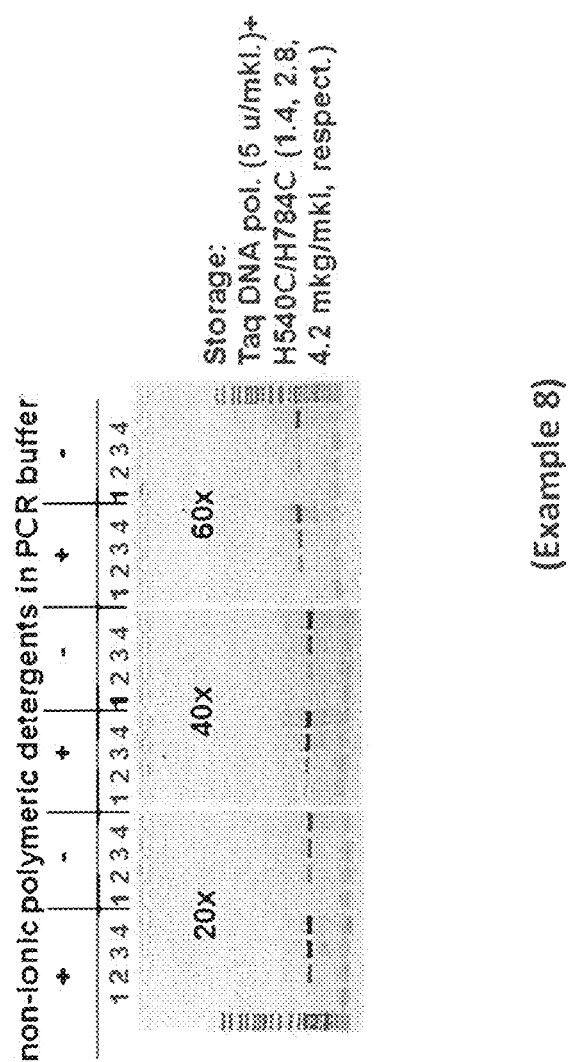
Figure 11D:
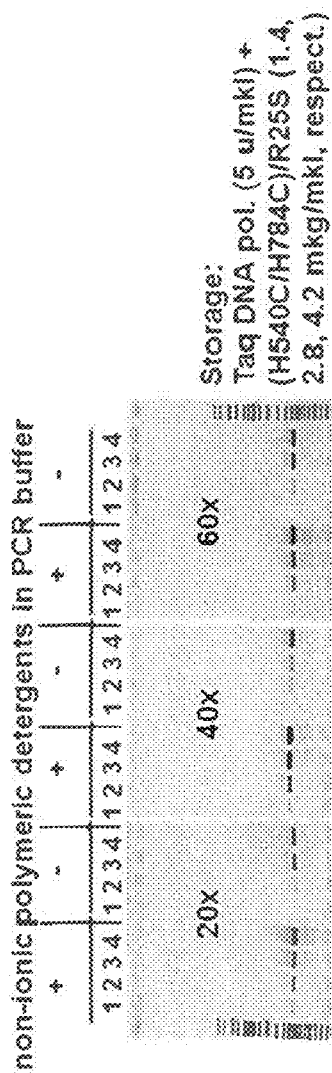

The experiments were performed as described in Example 4, except that Taq DNA polymerase stock solutions (~70 ng/mkl; 5 u/mkl) without detergents were prepared with increasing concentrations of inactive Taq DNA polymerase mutants K540C/H784C (FIG. 11B), (K540C/H784C)/Y81F (FIG. 11C), (K540C/H784C)/R25S (FIG. 11D) at weight ratios: 1:20, 1:40, 1:60. Commercial Taq DNA polymerase preparation was used as control (FIG. 11A). Amplification reactions were performed using 2.5 units of Taq DNA polymerase and different amounts (0.1, 1, 10, 100 ng) of human DNA in 50 mkl reaction buffer (FIG. 11).

Experimental results demonstrate similar performance (sensitivity and yield both for enzyme concentration and target DNA concentration) of Taq DNA polymerase/mutant mixes as compared with commercial Taq DNA polymerase preparation containing non-ionic polymeric detergents (FIG. 11, 12). Noteworthy, Taq DNA polymerase/mutant composition generated PCR products both in the presence and absence of non-ionic polymeric detergents although addition of non-ionic polymeric detergents resulted in slightly higher yield of PCR products (FIG. 11, 12).

Example 9: PCR Using Different Amounts of Taq DNA Polymerase in Taq/Mutant Compositions We have performed experiments to identify optimal effective Taq DNA polymerase concentration in PCR reaction using stabilized Taq DNA polymerase/mutant compositions as a source of the enzyme.

Figure 12A:
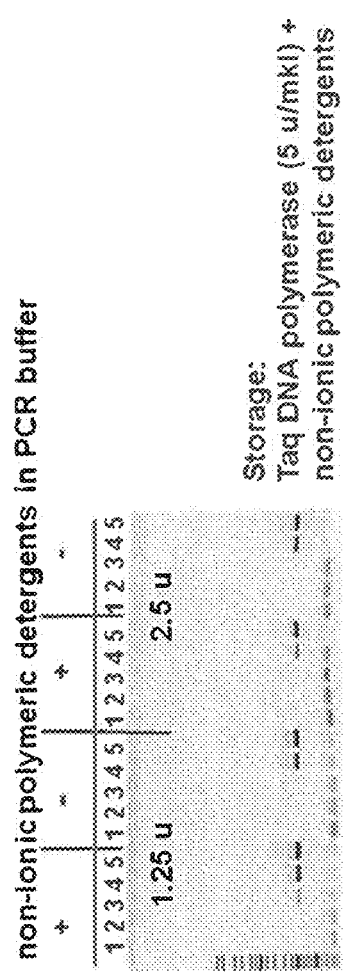

Experiments were performed as described in Example 4, except that Taq DNA polymerase (~70 ng/mkl; 5 u/mkl) stock solution was prepared with inert Taq DNA polymerase mutants K540C/H784C (FIG. 12B), (K540C/H784C)/Y81F (FIG. 12C), (K540C/H784C)/R25S (FIG. 12D) at weight ratios: 1:40 without any detergents. Commercial Taq DNA polymerase preparation was used as control (FIG. 12A). Amplification reactions were performed using 1.25 and 2.5 units of Taq DNA polymerase and different amounts (0.1, 1, 10, 100 ng) of human DNA in 50 mkl reaction buffer (FIG. 12).

Example 10: PCR Using Different Storage Compositions of Taq DNA Polymerase

We have tested a variety of non functional Taq DNA polymerase mutants for their ability to act as stabilizers of Taq DNA polymerase during PCR reaction when no surfactants are used. The experiments were performed as described in Example 12, except that stock solutions of Taq DNA polymerase (~70 ng/mkl; 5 u/mkl) were prepared using inert Taq DNA polymerase mutants H540C/D610A/H784C, R536C/H540C/D610A/H784C, N485S/R536C/H540C/H784C, I532T/R536C/H540C/H784C, (H540C/H784C)/(Y81F/G187A), (H540C/H784C)/(R25S/Y81F), (H540C/H784C)/(R25S/G187A) and (H540C/H784C)/(R25S/Y81F/G187A), (R536C/H540C/D610A/H784C)/(Y81F/G187A), (I532T/R536C/H540C/H784C)/(Y81F/G187A) and (I532T/R536C/H540C/H784C)/(R25S/Y81F/G187A) at weight ratios: 1:40 without any detergents. Amplification reactions were performed using 2.5 units of Taq DNA polymerase and 100 ng of human DNA in 50 mkl reaction buffer (FIG. 13).

Figure 13:
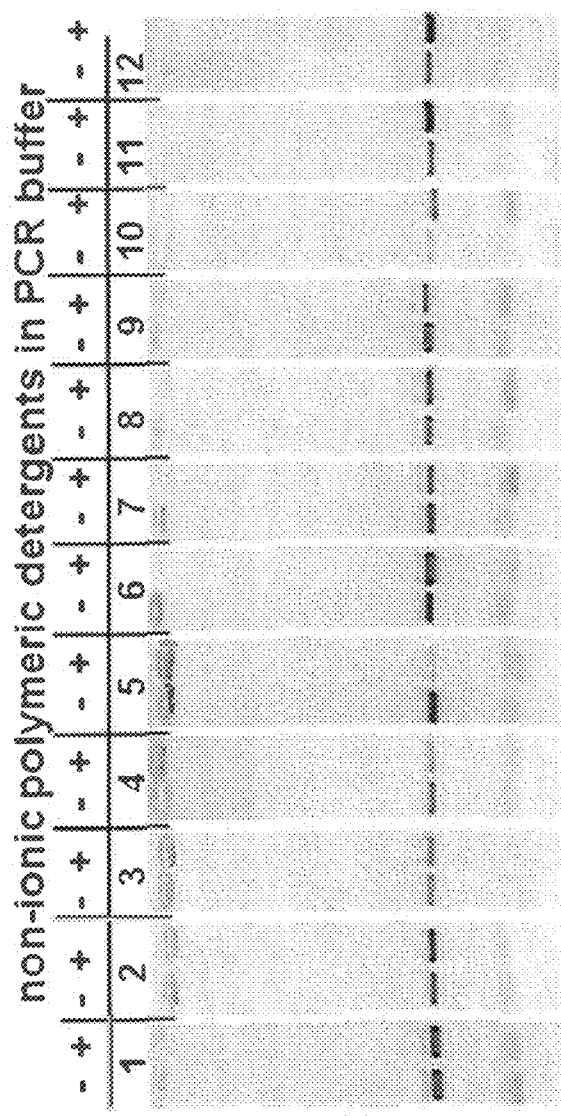

Our data indicate that all tested inactive Taq DNA polymerase mutants are also suitable for stabilizing Taq DNA polymerase in storage and reaction mixtures instead of surfactants (FIG. 13).

Example 11: Adhesion of Other Thermophilic DNA Polymerases to Polymeric Surfaces We have studied whether the adhesion of thermophilic DNA polymerases to the tube surface constitutes a more general phenomenon that causes the loss of stability of these enzymes when stored without non-ionic detergents. Recombinant *Thermococcus* sp. DNA polymerase (Gene Bank No. GQ891548) was chosen as a model enzyme for these experiments.

Recombinant *Thermococcus* sp. DNA polymerase was purified without the addition of any detergent in any step. Fractions containing the enzyme were pooled and dialyzed against storage buffer without non-ionic polymeric detergents (20 mM Tris-HCl, pH8.2 at 25° C.; 100 mM KCl, 1 mM DTT, 0.1 mM EDTA, 50% (v/v) glycerol). Enzyme concentration was estimated using Bradford Reagent. DNA polymerase and 3'-5' exonuclease activity assays were performed by measuring incorporation of [methyl-$^3$H]-dTTP into polynucleotide fraction or degradation of [$^3$H]-labelled polynucleotide.

Adsorption experiments of *Thermococcus* sp. DNA polymerase (~40 ng/mkl; 5 u/mkl) were performed in 1.5 ml micro test tubes as described in Example 3, except that *Thermococcus* sp. DNA polymerase stock solutions prepared in the storage buffer supplemented with 0.1% (v/v) Nonidet P40 and 0.1% (v/v) Tween 20 or without non-ionic polymeric detergents were used (FIG. 14) for comparison.

Figure 14:
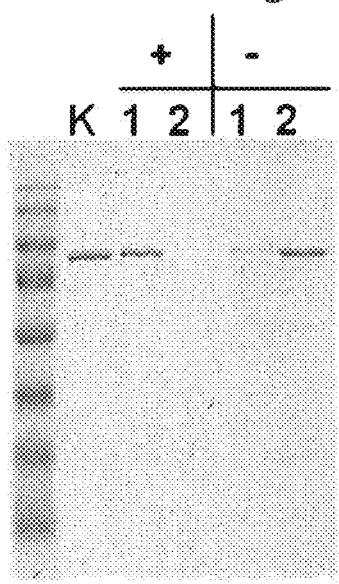
FIG. 14. (Example 11)
K—Taq DNA polymerase (5 u/mkl-~70 ng/mkl); 1—*Thermococcus* sp. DNA polymerase in solution; 2—adsorbed *Thermococcus* sp. DNA polymerase
FIG. 15. (Example 12)
1, 2, 3, 4, 5—0.5, 1, 2.5, 5, 10 u *Thermococcus* sp. DNA polymerase/50 mkl, respectively.

Experimental data confirm that other thermophilic DNA polymerases, e.g. *Thermococcus* sp. DNA polymerase, also are adsorbed on the plastic surface (FIG. 14). SDS gel analysis revealed that 1.5 ml micro test tube in the absence of detergents adsorbed 470 ng of *Thermococcus* sp. DNA polymerase while the enzyme was soluble in the same conditions when detergents were used.

Example 12: PCR Using *Thermococcus* sp. DNA Polymerase and Non-Ionic Polymeric Detergents We have tested whether non-ionic polymeric detergents are capable to stabilize *Thermococcus* sp. DNA polymerase during PCR.

Figure 15:
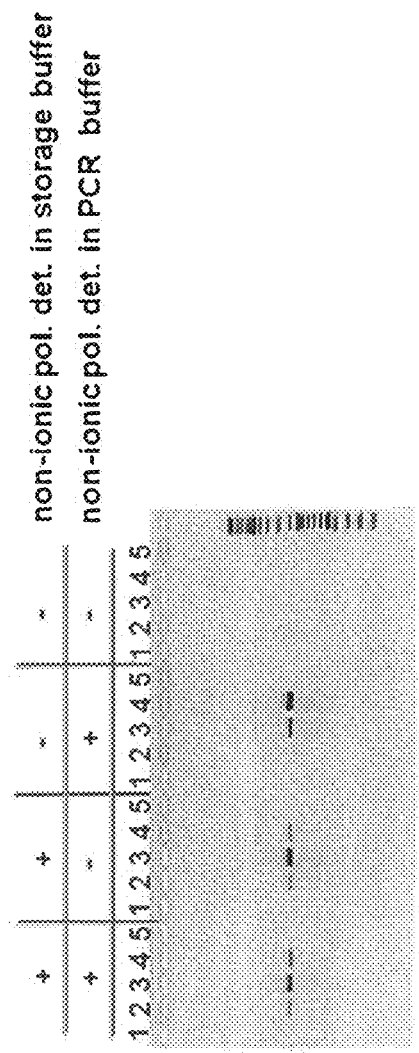

PCR was carried out in the Mastercycler (Eppendorf) using *Thermococcus* sp. DNA polymerase stock preparations stored in the presence or absence of non-ionic polymeric detergents (Example 14). Amplification reactions were performed using 0.5, 1, 2.5, 5, 10 units of *Thermococcus* sp. DNA polymerase in 50 mkl 1× reaction buffer (10×: 200 mM Tris-HCl, pH8.8 at 25° C.; 100 mM (NH$_4$)$_2$SO$_4$, 100 mM KCl, 20 mM MgSO$_4$, 1 mg/ml BSA) in the absence or presence of 0.1% (v/v) Triton X-100. Both buffers were supplemented with 0.2 mM dNTP, 0.2 µM of each M13/pUC sequencing primer and pTZ57R plasmid with 1 kb insert as template (1 ng/50 mkl). A 1 kb DNA fragment was amplified using M13/pUC sequencing primer (−46), 22-mer (5'-GCCAGGGTTTTCCCAGTCACGA) and M13/pUC reverse sequencing primer (−46), 24-mer (5'-GAGCGGATAACAATTTCACACAGG) (Fermentas). Components of PCR were mixed at room temperature and reactions were performed using the following cycling profiles: 95° C.—30 sec.; (95° C.—5 sec., 45° C.—10 sec., 72° C.—15 sec.)—25 cycles; 72° C.—5 min. After completion of PCR, the samples were mixed with 10 µl aliquots of the 6× MassRuler™ Loading Dye, and the samples were analyzed by gel electrophoresis in 0.7% agarose (FIG. 15).

Obtained data demonstrate that presence of detergents in at least one buffer (storage buffer or PCR buffer) is essential condition for PCR product generation by *Thermococcus* sp. DNA polymerase at conventionally used enzyme concentrations (FIG. 15).

Example 13: PCR Using *Thermococcus* sp. DNA Polymerase and Inactive Taq DNA Polymerase Mutants We have performed experiments to identify optimal effective *Thermococcus* sp. DNA polymerase concentration in PCR reaction using stabilized *Thermococcus* sp. DNA polymerase/mutant compositions as a source of the enzyme.

Experiments were performed as described in Example 15, except that reactions were carried out using 0, 1, 2.5, 5, 10 u of *Thermococcus* sp. DNA polymerase (without detergents) and 700 ng of Taq DNA polymerase mutant (K540C/H784C)/Y81F in 50 mkl reaction buffer (FIG. 16) in the presence or in the absence non-ionic polymeric detergents.

Figure 16:
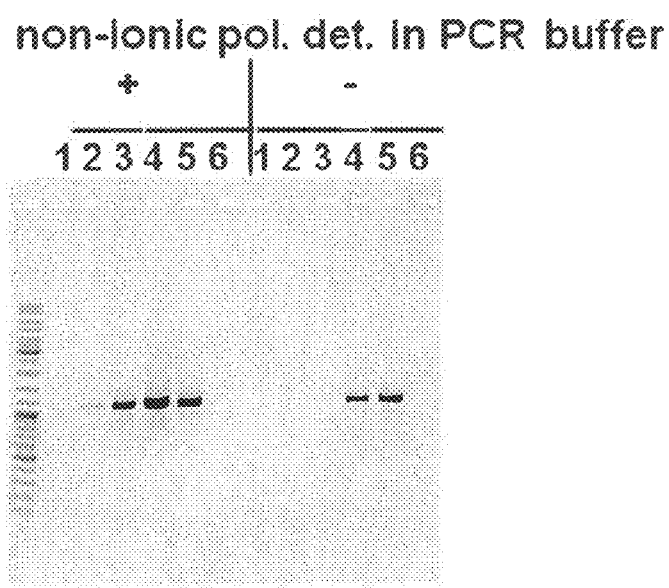
FIG. 16. (Example 13)
1, 2, 3, 4, 5, 6—700 ng (K540C/H784C)/Y81F/50 mkl+0, 0.5, 1, 2.5, 5, 10 u *Thermococcus* sp. DNA polymerase/50 mkl, respectively.

Like in case of results obtained with Taq DNA polymerase (FIG. 10) the PCR experiments demonstrate that excessive concentrations of mutant protein alone did not generate PCR products, while *Thermococcus* sp. DNA polymerase/mutant protein mixtures yielded PCR products both in the presence or absence of non-ionic polymeric detergents. However, presence of non-ionic polymeric detergents in the reaction resulted in higher yields of PCR products (FIG. 16).

These results indicate that *Thermococcus* sp. DNA polymerase and non-functional polymerase mutant may be stored separately and added to reaction mixture directly before PCR reaction. Besides, reaction could be performed successfully without using any surfactants, such as non-ionic polymeric detergents. Also, our data support the suggestion that *Thermococcus* sp. DNA polymerase may be stably stored in the presence of excess amounts of non-functional mutants of another thermostable polymerase.

Example 14: PCR Using Different Storage Compositions of *Thermococcus* sp. DNA Polymerase Stabilized by Addition of Inactive Taq DNA Polymerase Mutant We have performed experiments to identify optimal effective concentration of inactive Taq DNA polymerase mutant that would completely stabilize *Thermococcus* sp. DNA polymerase in PCR reaction.

Figure 17A:
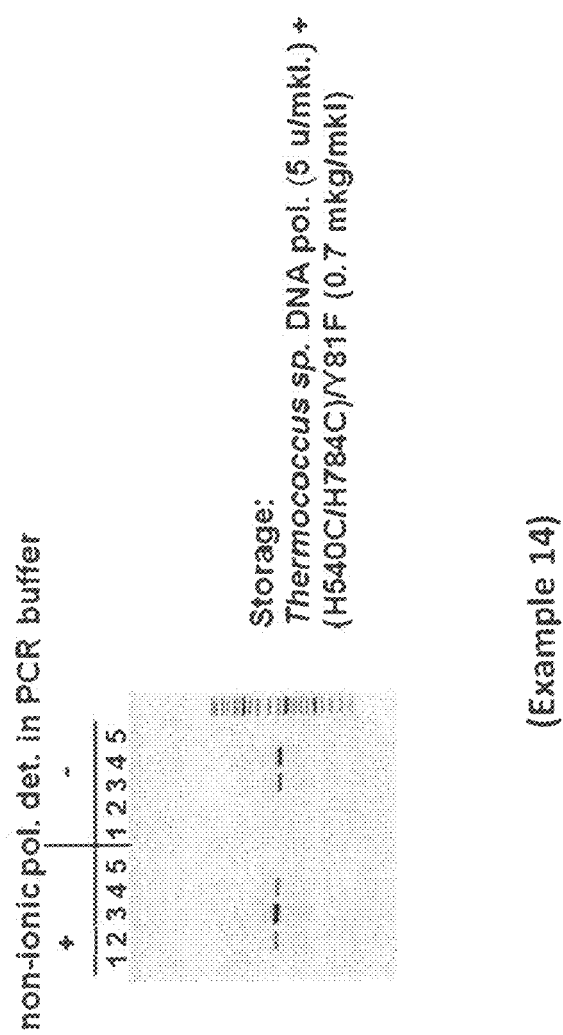
FIG. 17A-B. (Example 14)
A; B: 1, 2, 3, 4, 5-0.5, 1, 2.5, 5, 10 u *Thermococcus* sp. DNA polymerase/50 mkl, respectively
FIG. 18. (Example 15)
Stock solutions:
*Thermococcus* sp. DNA pol. (2.5 u/mkl.)
1, 2—+non-ionic polymeric detergents;
3, 4—without non-ionic polymeric detergents;
5, 6—+(R671S/K677S/K712S)/N210D (~0.76 mkg/mkl),
7, 8—+(R671E/K677E/K712E)/N210D (~0.76 mkg/mkl),
FIG. 19A-B. (Example 16)
qPCR was performed with Maxima™ Probe qPCR Master Mix (Fermentas) in the presence BSA (600 ng/mkl), (R536C/K540C/D610A/H784C)/(Y81F/G187A) (21 ng/mkl) or without any additional proteins in LyghtCycler 2.

The experiments were performed as described in Example 15, except that stock solutions of *Thermococcus* sp. DNA polymerase (5 u/mkl) without detergents were prepared by adding inactive Taq DNA polymerase mutant (K540C/H784C)/Y81F at 0.7 and 2.3 mkg/mkl concentrations (see FIGS. 17A and B, respectively).

Figure 17B:
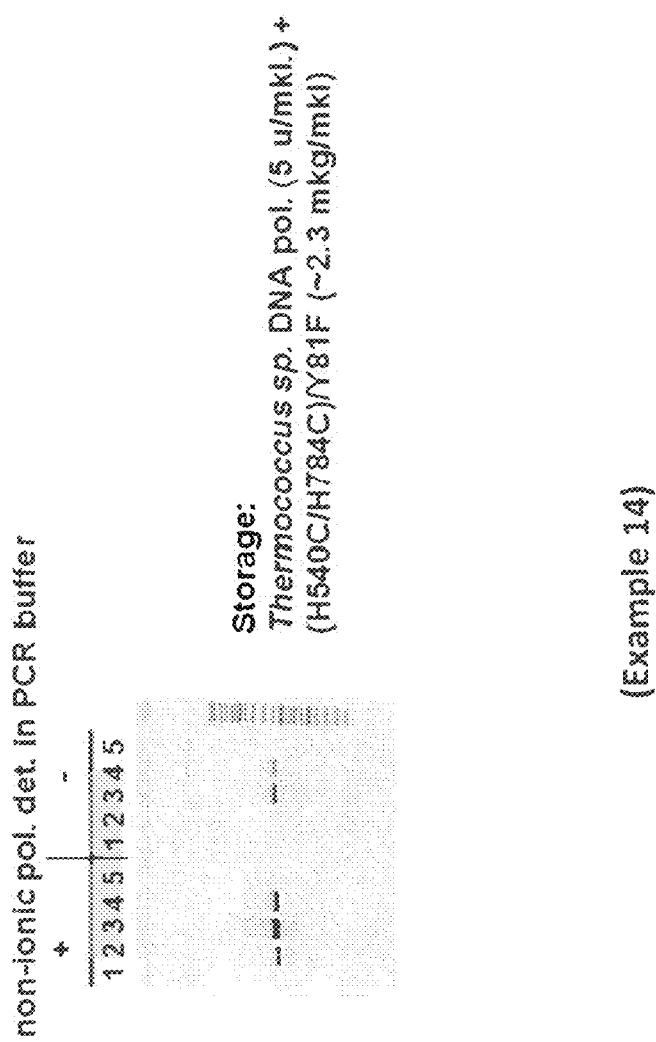

Like in case of PCR results obtained for Taq DNA polymerase (FIG. 11, 12), both stabilized *Thermococcus* sp. DNA polymerase compositions were capable of synthesizing PCR products both in the presence and absence of non-ionic polymeric detergents, however, addition of non-ionic polymeric detergents resulted in slightly higher yield of PCR products (FIG. 17).

Example 15: PCR Using Different Storage Compositions of *Thermococcus* sp. DNA Polymerase (Mixes with Inert *Thermococcus* sp. DNA Polymerase Mutant)

We have also tested whether non functional mutants of *Thermococcus* sp. DNA polymerase are capable to stabilize the active form of the same enzyme.

Targets for mutagenesis in polymerase active sites (N210, R671, K677, K712) were chosen based on 3D analysis of closely related thermophilic DNA polymerases: Tgo (PDB: 1TGO), D.Tok (PDB:1D5A), Kod1 (PDB:1WNS), Pfu (PDB:2JGU).

Site-directed mutagenesis was performed by the megaprimer method (Barik. (1995) *Mol. Biotechnol.* 3: 1-7) using pair of primers flanking the polymerase gene and the oligonucleotides encoding desired mutations. After cloning of PCR products into prepared vector the presence of required mutations, as well as the absence of additional mutations were confirmed by sequencing. *Thermococcus* sp. DNA polymerase mutants were purified in the absence of non-ionic polymeric detergents. Fractions containing the enzyme were pooled and dialyzed against storage buffer without non-ionic polymeric detergents (20 mM Tris-HCl, pH8.2 at 25° C.; 100 mM KCl, 1 mM DTT, 0.1 mM EDTA, 50% (v/v)

glycerol). Concentrations of mutant enzymes were estimated using Bradford Reagent (Fermentas) following manufacturer's recommendations.

Obtained mutant enzymes were assayed for DNA polymerase and 3'-5' exonuclease activity. DNA polymerase and 3'-5' exonuclease activity assays were performed by measuring incorporation of [methyl-$^3$H]-dTTP into polynucleotide fraction or degradation of [$^3$H]-labelled polynucleotide. DNA binding properties of Taq DNA polymerase mutants were investigated using electrophoretic mobility shift assay (EMSA) as described for Taq DNA polymerase in Example 7 and Example 8.

Summarized results on enzymatic activities and affinities of *Thermococcus* sp. DNA polymerase mutants to DNA are presented in Table 8.

TABLE 8

*Thermococcus* sp. DNA polymerase mutants.

| *Thermococcus* sp. DNA polymerase mutants | | *Thermococcus* sp. DNA polymerase mutants' activities | | Afinity for DNA ($K_d$, nM) | |
|---|---|---|---|---|---|
| polymerase act. site mut. | 3'-5' exonucl. act. site mut. | polymerase activity (%) | 3'-5' exoncl. activity (%) | Template-primer substr. | primer substr. |
| — | — | 100 | 100 | 2.8 ± 0.7 | 52 ± 17 |
| K712S | — | 120 | n.d. | n.d. | n.d. |
| K712E | — | 75 | n.d. | n.d. | n.d. |
| R671S/K677S | — | 26 | n.d. | n.d. | n.d. |
| R671E/K677E | — | 4 | n.d. | 240 ± 20 | 730 ± 70 |
| R671S/K677S/K712S | — | 2 | n.d. | 110 ± 20 | 310 ± 40 |
| R671E/K677E/K712E | — | ~0* | n.d. | 190 ± 20 | 740 ± 50 |
| R671E/K677E | N210D | 2 | ~0* | n.d. | n.d. |
| R671S/K677S/K712S | N210D | 2 | ~0* | 190 ± 20 | 440 ± 40 |
| R671E/K677E/K712E | N210D | ~0* | ~0* | 470 ± 20 | 2300 ± 200 |

*estimated activity was less than 0.1%.

To test whether inactive *Thermococcus* sp. DNA polymerase mutants can act as stabilizers for the active form of the same enzyme we have prepared several storage compositions by mixing *Thermococcus* sp. DNA polymerase (2.5 u/mkl) with 0.76 mkg/mkl concentrations of inactive *Thermococcus* sp. DNA polymerase mutants (R671S/K677S/K712S)/N210D or (R671E/K677E/K712E)/N210D.

Figure 18:
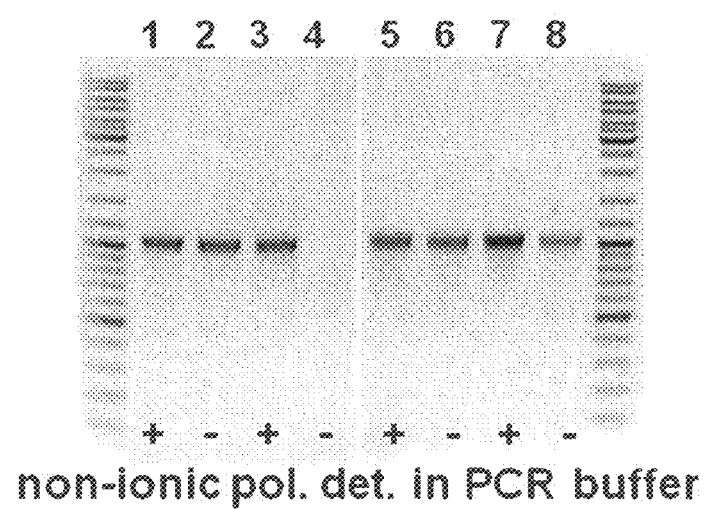

PCR was carried out in the Mastercycler (Eppendorf) using *Thermococcus* sp. DNA polymerase stock solutions stabilized as described above with or without non-ionic polymeric detergents (Example 14). Amplification reactions were performed using 2.5 units of *Thermococcus* sp. DNA polymerase in 50 mkl 1× reaction buffer (10×: 200 mM Tris-HCl, pH8.8 at 25° C.; 100 mM (NH$_4$)$_2$SO$_4$, 100 mM KCl, 15 mM MgSO$_4$, 1 mg/ml BSA) in the absence or presence of 0.1% (v/v) Triton X-100. Both buffers were supplemented with 0.2 mM dNTP, 0.5 µM of each PCR primer and plasmid pASK with 1.055 kb insert as template (5 ng/50 mkl). A 1.055 kb DNA fragment was amplified using pASK reverse (5'-CGCAGTAGCGGTAAACG-3') and agseq5 (5'-ATTCCCTCCATACTCGGGG-3') primers (Fermentas). Components of PCR were mixed at room temperature and reactions were performed using the following cycling profiles: 94° C.—2 min.; (94° C.—30 sec., 50° C.—30 sec., 72° C.—20 min)—30 cycles. After completion of PCR, the samples were mixed with 10 µl aliquots of the 6× MassRuler™ Loading Dye and analyzed by gel electrophoresis in 0.7% agarose (FIG. 18).

Obtained results confirm our presumption that non functional mutants of *Thermococcus* sp. DNA polymerase are capable to stabilize active form of the same enzyme both during storage and in the reaction mixture without the use of non-ionic polymeric detergents (FIG. 18).

Example 16: qPCR in the Presence of Non-Functional Taq DNA Polymerase Mutant

Stabilizing effect of inactive polymerase mutants in thermophilic polymerase composition presents the possibility to use such mutants in one more application, namely, to use such mutants instead of BSA in quantitative real-time PCR. The use of native BSA in qPCR mixtures is known in the art (Steuerwald et al (1999) *Mol Hum Reprod.* 5(11):1034-9.) and several companies produce commercial qPCR master mixtures that contain BSA.

The use of native BSA in molecular biology reagents compositions has certain disadvantages similar to those posed by products of animal origin. Use of products of animal origin in diagnostics and biotechnology applications is undesirable due to possible contamination of products with animal DNA or proteinaceous infectious agents. Numerous countries have introduced special import regimes for products that contain proteins of animal origin, especially if proteins originate from beef or calf. In addition, BSA is not a thermostable protein, therefore its stabilizing effect should not last longer than the first denaturation step. Therefore possibility to replace BSA with thermostable substitute in PCR reactions presents useful improvement of this technology.

Quantitative real-time PCR experiments were performed using LyghtCycler 2 Real-Time PCR System instrument (Roche). Reactions were performed in the presence of BSA or R536C/K540C/D610A/H784C)/(Y81F/G187A) mutant, or in the absence of any additional proteins.

Total RNA was isolated from Jurkat cells using RNeasy Mini kit (Qiagen) according to manufacturer's recommendations. Five dilutions of total RNA preparation (ranging from 100 ng to 10 pg) were used for cDNA synthesis with RevertAid™ Premium Reverse Transcriptase (Fermentas). The mix of oligo (dT)$_{18}$ and random primers at 25 pmol each per 20 µl reaction were used to prime reverse transcription following manufacturer's protocol for reverse transcription reaction as a first step in two-step qRT-PCR.

Quantitative RT-PCR's were performed in duplicates for each sample using 2 µl of the cDNA reaction supplemented with 0.3 µM PGK1_direct (5'-AGCTGCTGGGTCTGT-CATCCT-3') and 0.3 µM PGK1_reverse (5'-ATCTTTTC-CCTTCCCTTCTTCCT-3') primers (both from MWG) specific for human PGK gene, 0.2 µM FAM-TAMRA PGK_probe (5'-TGGAGAACCTCCGCTTTCATGT-3') (Metabion) and Maxima™ Probe qPCR Master Mix (Fermentas) in a reaction of 20 µl.

The samples were prepared with BSA (at final concentration of 600 ng/mkl) or R536C/K540C/D610A/H784C)/(Y81F/G187A) (at final concentration of 21 ng/mkl) or without any additional proteins and reactions were performed in LyghtCycler 2 Real-Time PCR System instrument (Roche) using the following cycling profile: 95° C.—10 min; (95° C.—0.25 min, 60° C.—1 min)—40 cycles.

Amplification efficiency was determined from the slope of log-linear portion of the calibration curve obtained from the serially diluted total RNA solutions. Specifically, PCR efficiency equals to $10^{-1/slope}-1$, when the logarithm of initial template concentration (independent variable) is plotted on x axis and $C_q$ (quantification cycle, previously known as the crossing point ($C_p$), the threshold ($C_t$), or take-off point (TOP)) is plotted on y axis.

Quantitative real-time PCR data show that inactive Taq mutant is efficient replacement of BSA. Estimated amplification efficiency was very close to theoretical maximum (100%) in the presence of either BSA or inactive Taq polymerase mutant protein (Table 9). Theoretical maximum 1 (or 100%) indicates that the amount of product doubles with each cycle.

TABLE 9 qPCR efficiency.

| Quantitative real-time PCR | PCR efficiency (%) |
|---|---|
| Without additional proteins | 87 |
| In the presence of BSA | 103 |
| In the presence of inactive Taq mutant | 106 |

In addition to comparable qPCR efficiencies obtained in the presence of BSA or inactive Taq mutant, qPCR data demonstrate that addition of inactive Taq mutant has positive influence on $C_q$ (quantification cycle) parameter and total yield of PCR products.

Figure 19A:
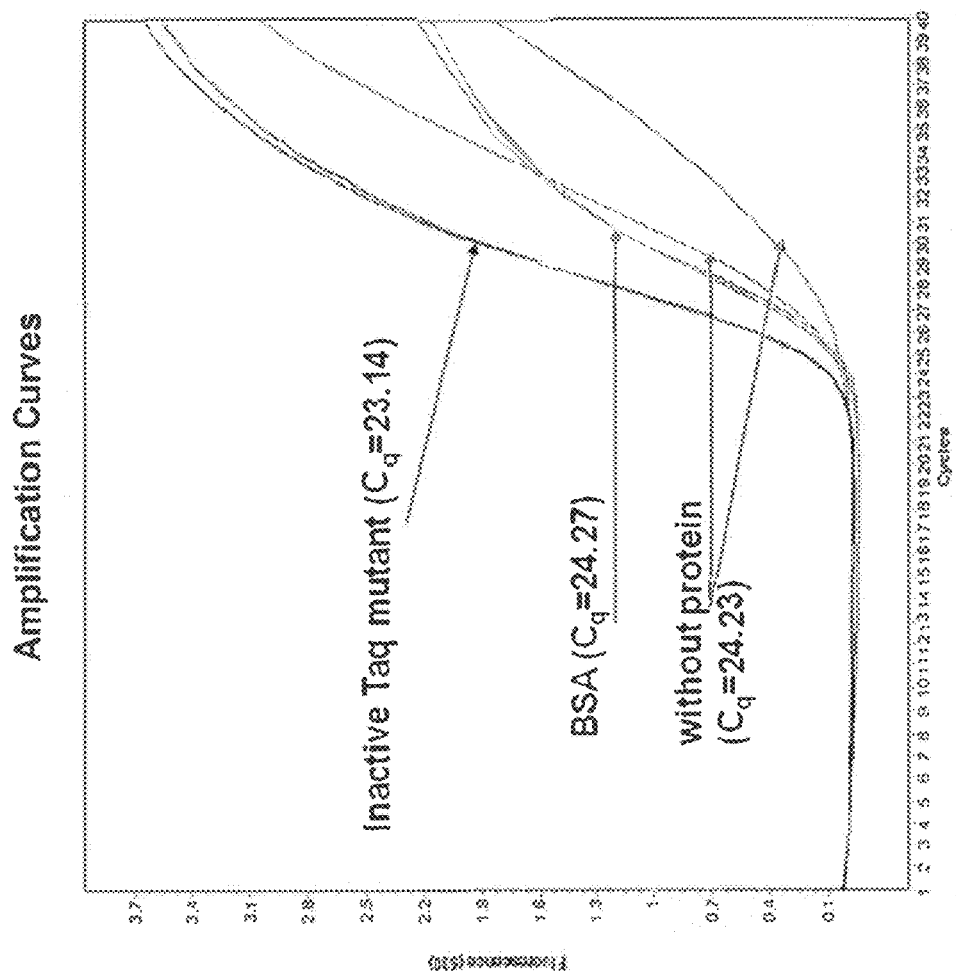
Figure 19B:
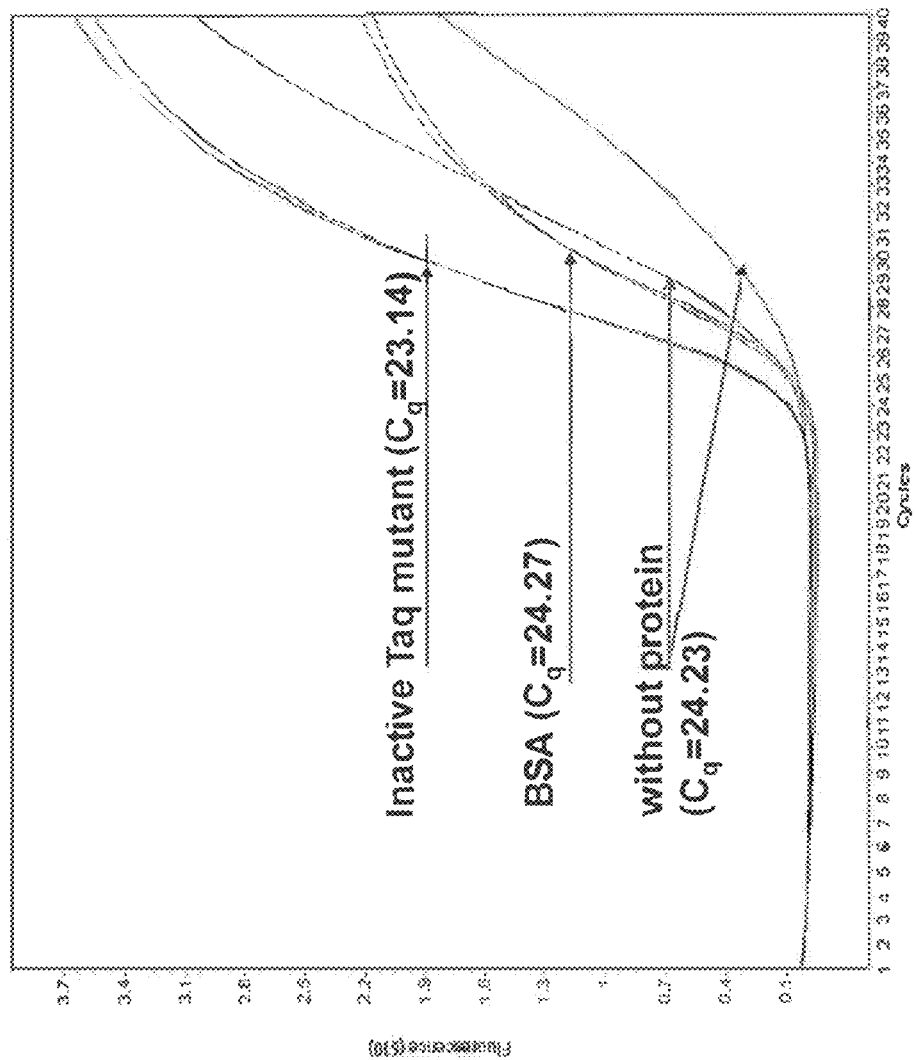

Representative curves of RT-qPCR (using 100 ng RNA) are presented in FIG. 19. In our experiments $C_q$ in the presence of inactive Taq polymerase mutant was 23, while in the case of BSA or in the absence of any additional protein—24. Our data also show that amplification curve in the presence of inactive Taq mutant is 1.5-fold higher than that obtained when BSA is used, what indicates that presence of inactive Taq mutant increases the yield of PCR products, possibly due to longer stabilizing effect on Taq polymerase during cycling reaction or better neutralisation of possible inhibitors in qRT-PCR.

In general, PCR may be inhibited by different materials interacting with DNA or DNA polymerase or it cofactor, Mg2+ ions. The PCR inhibitors may come from common test samples, such as: tissues (e.g. collagen, myoglobin), hair and skin (melanin, eumelanin), et al (www.promega.com/profiles/1001/ProfilesinDNA_1001_09.pdf). The addition of non-functional protein, such as BSA, most possibly due to competitive titration of these inhibitors, can stabilize the polymerisation reaction mixture and contribute to some resistance to inhibitors (Randstrom et al. (2004) *Molecular Biotechnology* 26: 133-145). Here we experimentally demonstrate that inactive Taq mutant may act as efficient "stabilizer" in amplifying DNA from complex biological samples.

Example 17: Neutralization of Hair Lysate Inhibitors in PCR by Addition of Non-Functional Taq DNA Polymerase Mutant Initially, possibility to neutralize sample inhibitory effect was tested using hair lysate. Hair lysate was prepared with Fast tissue-to-PCR Kit (Fermentas UAB).

Figure 20:
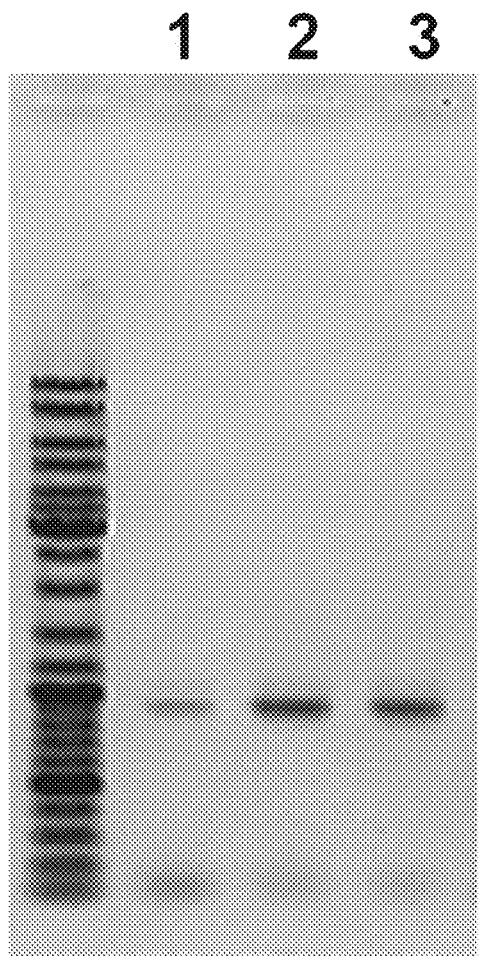
FIG. 20. (Example 17)
Taq DNA polymerase 2.5 u/50 mkl:
1—without additional protein;
2—+BSA (600 ng/mkl);
3—+(R536C/K540C/D610A/H784C)/(Y81F/G187A) (21 ng/mkl).

The reactions were performed as described in Example 4, except that 2.5 units of commercial Taq DNA polymerase were used in 50 mkl 1× reaction buffer (10×: 750 mM Tris-HCl, pH8.8 at 25° C.; 200 mM $(NH_4)_2SO_4$), 0.01% (v/v) Tween 20) supplemented with 4 mkl of hair lysate: (i) without additional proteins (FIG. 20; lane 1); (ii) in the presence of BSA (at final concentration of 600 ng/mkl) (FIG. 20, lane 2); (iii) in the presence of (R536C/K540C/D610A/H784C)/(Y81F/G187A) (at final concentration of 21 ng/mkl) (FIG. 20; lane 3).

Experimental results demonstrate that presence of either BSA, or non-functional Taq DNA polymerase mutant increase PCR yield in comparison to the sample without any stabilizing protein additives.

Example 18: Neutralisation of Tissue Lysate Inhibitors in PCR by Addition of Non-Functional Taq DNA Polymerase Mutant Next series experiments were performed testing another complex biosamples—mouse ear (FIG. 20; A, B) and tail (FIG. 21; C, D) tissue lysates.

PCR was carried out in the Mastercycler (Eppendorf). The amplification reactions were performed using Maxima Hot Start Green PCR Master Mix (2×) in the presence of BSA (FIG. 21; lines 2, 3) or (R536C/K540C/D610A/H784C)/(Y81F/G187A) mutant (FIG. 21; lines 5, 6), or in the absence of any additional proteins (FIG. 21, line 1). The reaction mixtures were supplemented with 0.5 mkM of each PCR primer and 1 (FIG. 21; A, C) or 4 mkl (FIG. 21; B, D) of mouse ear or tail tissue lysates, prepared using Fast tissue-to-PCR Kit (Fermentas UAB). A 1.1 kb DNA fragment was amplified with PCR primers: HPRT-3' (5'-GCTG-GTGAAAAGGACCTCT-3') and HPRT-5' (5'-CACAG-GACTAGAACACCTGC-3'). Components of PCR reaction were mixed at room temperature and reactions were performed using the following cycling profiles: 95° C.—3 min; (95° C.—20 s, 65° C.—30 s, 72° C.—1 min)—30 cycles; 72° C.—3 min. After reaction the samples were mixed with aliquots (10 μl) of the 6× MassRuller™ Loading Dye (Fermentas), and the samples were analyzed by gel electrophoresis in 1% agarose. The GeneRuler™ Express DNA Ladder (Fermentas) was used for evaluation of the amplicon size. Electrophoresis was performed in the 1×TBE buffer (89 mM Tris, 89 mM $H_3BO_3$, and 1 mM EDTA) at 5 V/cm for 75 min. After completion of electrophoresis, gels were stained with ethidium bromide (0.5 μg/ml) and destained afterwards in MiliQ-quality water for 20 minutes. After electrophoresis DNA bands were visualized by Ultra Lum Electronic U.V. Transilluminator (Ultra-Lum) (FIG. 21).

The PCR data clearly demonstrate that in testing of samples of mouse ear and tail tissue lysates, amplification yield in the presence of inactive Taq mutant (FIG. 21; lines 5, 6) is significantly higher than that obtained when BSA is used (FIG. 21; lines 2, 3) or without any additional stabilizer protein (FIG. 21; line 1). This indicates that presence of inactive Taq mutant exhibits superior neutralizing effect for inhibitors coming from tissue in PCR if compared to BSA, possibly due to more efficient competitive titration of the inhibitors. One could assume that better results in the presence of inactive Taq mutant were obtained due to bigger physical similarity of mutant to WT protein and higher thermostability in comparison to BSA.

The invention claimed is:

1. A method of stabilizing an active nucleic acid polymerase against loss of polymerase activity, comprising:
contacting the active nucleic acid polymerase with an amount of a mutant nucleic acid polymerase so as to stabilize the active nucleic acid polymerase, wherein:
the amount of the mutant nucleic acid polymerase is greater than the amount of active nucleic acid polymerase;
the active nucleic acid polymerase comprises a family A or family B thermophilic polymerase catalytic domain;
the mutant nucleic acid polymerase comprises a family A or family B polymerase catalytic domain and has reduced nucleic acid synthesis activity, reduced substrate binding activity, similar thermostability, and similar enzyme surface hydrophobicity compared to its corresponding wild type nucleic acid polymerase.

2. A The method according to claim 1, wherein the active nucleic acid polymerase is in a composition free of detergent.

3. A method of stabilizing an active nucleic acid polymerase against loss of polymerase activity, which comprises contacting the active nucleic acid polymerase with an amount of a mutant nucleic acid polymerase so as to stabilize the active nucleic acid polymerase, wherein the mutant nucleic acid polymerase protein is a mutant of the active nucleic acid polymerase, wherein the amount of the mutant nucleic acid polymerase is greater than the amount of active nucleic acid polymerase;
the active nucleic acid polymerase comprises a family A or family B thermophilic polymerase catalytic domain;
the mutant nucleic acid polymerase has reduced nucleic acid synthesis activity, reduced substrate binding activity, similar thermostability, and similar enzyme surface hydrophobicity compared to the active nucleic acid polymerase.

4. A The method according to claim 1, wherein the nucleic acid is DNA.

5. A method of stabilizing an active nucleic acid polymerase against loss of polymerase activity, which comprises contacting the active nucleic acid polymerase with an amount of a mutant nucleic acid polymerase so as to stabilize the active nucleic acid polymerase, wherein the active nucleic acid polymerase is a thermophilic nucleic acid polymerase, wherein both the active nucleic acid polymerase and the mutant nucleic acid polymerase are thermostable, and wherein:
the amount of the mutant nucleic acid polymerase is greater than the amount of active nucleic acid polymerase;
the active nucleic acid polymerase comprises a family A or family B polymerase catalytic domain;
the mutant nucleic acid polymerase comprises a family A or family B polymerase catalytic domain and has reduced nucleic acid synthesis activity, reduced substrate binding activity, similar thermostability, and similar enzyme surface hydrophobicity compared to its corresponding wild type nucleic acid polymerase.

6. The method according to claim 1, wherein the active nucleic acid polymerase is a bacterial or archeal nucleic acid polymerase.

7. The method according to claim 1, wherein the thermophilic polymerase is a Taq DNA polymerase or a *Thermococcus* sp. DNA polymerase.

8. A The method according to claim 1, wherein the mutant nucleic acid polymerase does not bind to the substrate for the active nucleic acid polymerase.

9. The method according to claim 1, wherein the active nucleic acid polymerase is stabilized in a storage composition, and/or the active nucleic acid polymerase is thermostable.

10. The method according to claim 1, wherein the active nucleic acid polymerase is stabilized in a reaction mixture for use in a reaction involving nucleic acid polymerase activity.

11. The method according to claim 1, wherein the active nucleic acid polymerase is stabilized against an enzyme inhibitor.

12. The method of claim 1, further comprising preparing a kit comprising the active nucleic acid polymerase and the mutant nucleic acid polymerase.

13. The method of claim 3, further comprising preparing a kit comprising the active nucleic acid polymerase and the mutant nucleic acid polymerase.

14. The method of claim 5, further comprising preparing a kit comprising the active nucleic acid polymerase and the mutant nucleic acid polymerase.

15. The method of claim 3, wherein the mutant nucleic acid polymerase does not bind to the substrate of the active nucleic acid polymerase.

16. The method of claim 5, wherein the mutant nucleic acid polymerase does not bind to the substrate of the active nucleic acid polymerase.

17. The method of claim 3, wherein the active nucleic acid polymerase is stabilized in a storage composition, and/or the active nucleic acid polymerase is thermostable.

18. The method of claim 5, wherein the active nucleic acid polymerase is stabilized in a storage composition.

19. The method according to claim 5, wherein the active nucleic acid polymerase is a bacterial or archeal nucleic acid polymerase.

20. The method according to claim 5, wherein the thermophilic nucleic acid polymerase is a Taq DNA polymerase or a *Thermococcus* sp. DNA polymerase.

* * * * *